(12) United States Patent
Abraham et al.

(10) Patent No.: US 11,655,481 B2
(45) Date of Patent: May 23, 2023

(54) METHODS FOR NUCLEAR REPROGRAMMING USING SYNTHETIC TRANSCRIPTION FACTORS

(71) Applicant: LONZA WALKERSVILLE, INC., Walkersville, MD (US)

(72) Inventors: Eytan Abraham, Potomac, MD (US); Thomas Payne, Cambridge (GB); Robert J. Young, London (GB); Inbar Friedrich Ben Nun, Rockville, MD (US)

(73) Assignee: LONZA WALKERSVILLE, INC., Walkersville, MD (US)

( * ) Notice: Subject to any disclaimer, the term of this patent is extended or adjusted under 35 U.S.C. 154(b) by 540 days.

(21) Appl. No.: 16/844,723

(22) Filed: Apr. 9, 2020

(65) Prior Publication Data
US 2020/0385755 A1    Dec. 10, 2020

Related U.S. Application Data

(63) Continuation of application No. 15/180,190, filed on Jun. 13, 2016, now abandoned.

(60) Provisional application No. 62/175,111, filed on Jun. 12, 2015.

(51) Int. Cl.
| | |
|---|---|
| *C12N 15/85* | (2006.01) |
| *C12N 5/074* | (2010.01) |
| *A61K 35/15* | (2015.01) |
| *A61K 35/33* | (2015.01) |
| *A61K 35/51* | (2015.01) |
| *G01N 33/50* | (2006.01) |
| *A61K 35/12* | (2015.01) |

(52) U.S. Cl.
CPC ............. *C12N 15/85* (2013.01); *A61K 35/12* (2013.01); *A61K 35/15* (2013.01); *A61K 35/33* (2013.01); *A61K 35/51* (2013.01); *C12N 5/0696* (2013.01); *G01N 33/5073* (2013.01); *C12N 2501/40* (2013.01); *C12N 2501/602* (2013.01); *C12N 2501/603* (2013.01); *C12N 2501/604* (2013.01); *C12N 2501/606* (2013.01); *C12N 2501/608* (2013.01); *C12N 2506/11* (2013.01); *C12N 2510/00* (2013.01)

(58) Field of Classification Search
CPC ...................................................... C12N 15/85
See application file for complete search history.

(56) References Cited

U.S. PATENT DOCUMENTS

| | | |
|---|---|---|
| 2013/0065814 A1 | 3/2013 | Xu et al. |
| 2014/0068797 A1 | 3/2014 | Doudna et al. |
| 2014/0273037 A1 | 9/2014 | Wu |
| 2014/0273226 A1 | 9/2014 | Wu |
| 2014/0295556 A1 | 10/2014 | Joung et al. |
| 2014/0295557 A1 | 10/2014 | Joung et al. |
| 2014/0349405 A1 | 11/2014 | Sontheimer et al. |
| 2015/0045546 A1 | 2/2015 | Siksnys et al. |
| 2015/0071898 A1 | 3/2015 | Liu et al. |
| 2015/0071899 A1 | 3/2015 | Liu et al. |
| 2015/0071906 A1 | 3/2015 | Liu et al. |

FOREIGN PATENT DOCUMENTS

WO        2014172470 A2        10/2014

OTHER PUBLICATIONS

Gilbert et al. "CRISPR-Mediated Modular RNA-Guided Regulation of Transcription in Eukaryotes" Cell. Jul. 18, 2013 154: 442-451 (Year: 2013).*
Pablo Ross. (BD Biosciences Research Grant Program. 2014 Research Grant Program Winning Abstract. "Induction of Pluripotency by CRISPR-Cas9 Epigenetic Engineering", published online Feb. 26, 2015). (Year: 2015).*
Li et al. (Nature Letters. Aug. 27, 2009; 460: 1136-1139 and Supplemental Methods) (Year: 2009).*
Ramos-Mejia et al (PLoS One 7(4): e35824, pp. 1-11 [2012]). (Year: 2012).*
International Search Report for WO 2016/201399 (PCT/US2016/037141), dated Sep. 1, 2016.
Written Opinion of the International Search Authority for WO 2016/201399, dated Sep. 1, 2016.
Barrangou and Marraffini, CRISPR-Cas systems: prokaryotes upgrade to adaptive immunity, Molecular Cell, 2014, 54 (2):234-244.
Balboa et al., Conditionally stabilized dCas9 activator for controlling gene expression in human cell reprogramming anti differentiation. Stem Cell Reports, 2015, 5(3):448-459.
Charkraborty et al., A CRISPR/Cas9-based system for reprogramming cell lineage specification, Stem Cell Reports, 2014, 3(6):940-947.
Chavez et al., Highly efficient Cas9-mediated transcriptional programming, Nature Methods, 2015, 12(4):326-328.

(Continued)

*Primary Examiner* — Scott Long
(74) *Attorney, Agent, or Firm* — Medler Ferro Woodhouse & Mills PLLC

(57) ABSTRACT

The current disclosure provides methods for reprogramming mammalian somatic cells by regulating the expression of endogenous cellular genes. Cellular reprogramming of somatic cells can be induced by activating the transcription of embryonic stem cell-associated genes (e.g., oct3/4) and suppressing the transcription of somatic cell-specific and/or cell death-associated genes. The endogenous transcription machinery can be modulated using synthetic transcription factors (activators and suppressors), to allow for faster, and more efficient nuclear reprogramming under conditions amenable for clinical and commercial applications. The current disclosure further provides cells obtained from such methods, along with therapeutic methods for using such cells for the treatment of diseases amendable to stem cell therapy, as well as kits for such uses.

9 Claims, 4 Drawing Sheets

(56) References Cited

OTHER PUBLICATIONS

Chen et al., Rapamycin and other longevity-promoting compounds enhance the generation of mouse induced pluripotent stem cells, Aging Cell, 2011, 10(5):908-911.
Cong et al., Multiplex genome engineering using CRISPR/Cas systems, Science, 2013, 339(6121):819-823.
Fu et al., Improving CRISPR-Cas nuclease specificity using truncated guide RNAs, Nature Biotechnology, 2014, 32 (3):279-284.
Gaj et al., ZFN, TALEN, and CRISPR/Cas-based methods for genome engineering, Trends in Biotechnology, 2013, 31 (7):397-405.
Gilbert et al., CRISPR-mediated modular RNA-guided regulation of transcription in eukaryotes, Cell, 2013, 154 (2):442-451.
Huangfu et al., Induction of pluripotent stem cells by defined factors is greatly improved by small-molecule compounds, Nature Biotechnology, 2008, 26(7):795-797.
Ieda et al., Direct reprogramming of fibroblasts into functional cardiomyocytes by defined factors, Cell, 2010, 142 (3):375-386.
Jinek et al., A programmable dual-RNA-guided DNA endonuclease in adaptive bacterial immunity, Science, 2012, 337:816-821.
Kearns et al., Cas9 effector-mediated regulation of transcription and differentiation in human pluripotent stem cells, Development, 2014, 141(1):219-223.
Kim et al., Highly efficient RNA-guided genome editing in human cells via delivery of purified Cas9 ribonucleoproteins, Genome Res, 2014, 24(6):1012-1019.
Konermann et al., Genome-scale transcriptional activation by an engineered CRISPR-Cas9 complex, Nature, 2015, 517(7536):583-588.
Li et al., The Ink4/Arf locus is a barrier for iPS cell reprogramming, Nature, 2009, 460(7259):1136-1139.
Li, Duo, Endogenous OCT4 gene activation by artificial transcription factors in mouse embryonic fibroblast, China Excellent Master thesis Full-text Database: Basic Science Series, 2015, Issue 2 (relevant part only with English Abstract).
Mali et al., RNA-guided human genome engineering via Cas9, Science, 2013, 339(6121):823-826.
Mali et al., CAS9 transcriptional activators for target specificity screening and paired nickases for cooperative genome engineering, Nature Biotehcnology, 2013, 31(9):833-838.
Okita et al., A more efficient method to generate integration-free human iPS cells, Nature Methods, 2011, 8:409-412.
Okita et al., An efficient nonviral method to generate integration-free human-induced pluripotent stem cells from cord blood and peripheral blood cells, Stem Cells, 2013, 31:458-466.
Ramos-Mejia et al., Residual expression of the reprogramming factors prevents differentiation of iPSC generated from human fibroblasts and cord blood CD34+ progenitors, PLoS One, 2012, 7(4):e35824.
Ross, Pablo, Induction of pluripotency by CRISPER-Cas9 epigenetic engineering, 2014 Research Grant Program Winning Abstract, 2014.
Sander and Joung, CRISPR-Cas systems for editing, regulating and targeting genomes, Nature Biotechnology, 2014, 32(4):347-355.
Shi et al., Induction of pluripotent stem cells from mouse embryonic fibroblasts by Oct4 and Klf4 with small-molecule compounds, Cell Stem Cell, 2008, 3(5):568-574.
Wu, Molecular and epigenetic mechanisms of cellular reprogramming mediated by transcription factors, Progress of Anatomical Science, 2014, 20(5):463-465, 473. (with English Abstract).
Xiao et al., Progress on mechanisms on reprogramming of somatic cells in mammals, Chinese Journal of Animal Husbandry, 2013, 49(9):82-88. (with English Abstract).
Yamanaka et al., Nuclear reprogramming to a pluripotent state by three approaches, Nature, 2010,465(7299): 704-712.
Zhang et al., Reprogramming of somatic cells via TAT-mediated protein transduction of recombinant factors, Biomaterials, 2012, 33(20):5047-5055.

\* cited by examiner

METHODS FOR NUCLEAR REPROGRAMMING USING SYNTHETIC TRANSCRIPTION FACTORS

FIELD OF THE INVENTION

The invention relates to methods of nuclear reprogramming of mammalian somatic cells to produce induced pluripotent stem cells (iPSCs).

BACKGROUND OF THE INVENTION

Cellular reprogramming, also referred to as nuclear reprogramming, is the process of generating stem cells, e.g., iPSCs from somatic cells. The derivation of iPSCs from numerous normal and diseased cell sources has revolutionized stem cell biology, and has enabled the generation of stem cells for eventual use in cell therapy and regenerative medicine.

iPSCs can be differentiated to many cell types, obviating the need to use discarded embryos from in vitro fertilization procedures to generate embryonic stem cells (ESCs) and minimizes the ethical issues involved. In addition, while ESCs can be only used for allogeneic cell therapy applications, iPSCs can be applied to both allogeneic and autologous cell therapy applications.

Seminal studies by Yamanaka and colleagues revealed that ectopic expression of certain transcriptional factors could induce pluripotency in somatic cells. These induced pluripotent stem cells self-renew and can differentiate into a wide variety of cell types. They have been used to successfully model human disease and have great potential for use in drug screening and cell therapy. However, much remains to be understood about the underlying mechanisms of reprogramming of somatic cells to iPSCs, and there is concern regarding potential clinical applications in the absence of mechanistic insights.

Reprogramming factors (RFs) used to reprogram somatic cells to pluripotency include Oct3/4, Sox2, c-Myc, Klf4, Lin28, and Nanog. Oct3/4 and Sox2 are transcription factors that maintain pluripotency in embryonic stem (ES) cells while Klf4 and c-Myc are transcription factors thought to boost iPSC generation efficiency. The transcription factor c-Myc is believed to modify chromatin structure to allow Oct3/4 and Sox2 to more efficiently access genes necessary for reprogramming while Klf4 enhances the activation of certain genes by Oct3/4 and Sox2. Nanog, like Oct3/4 and Sox2, is a transcription factor that maintains pluripotency in ES cells while Lin28 is an mRNA-binding protein thought to influence the translation or stability of specific mRNAs during differentiation. It has also been shown that retroviral expression of Oct3/4 and Sox2, together with co-administration of valproic acid, a chromatin destabilizer and histone deacetylase inhibitor, is sufficient to reprogram fibroblasts into iPSCs.

Several classes of vectors have been shown to induce pluripotency when overexpressing the requisite gene combinations. The earliest vectors relied on DNA-integrating retroviruses and transposons for nuclear reprogramming. Retrovirus-mediated reprogramming has the advantage of reasonably high reprogramming efficiency and high success rate, but raise concerns about potential tumorigenicity either by insertional mutagenesis or re-expression of oncogenic reprogramming factors. While Cre-LoxP site gene delivery or PiggyBac transposon approaches have been used to excise foreign DNA from the host genome following gene delivery, neither strategy eliminates the risk of mutagenesis because they leave a small insert of residual foreign DNA.

As an alternative to genetic modification, mRNA, episomal DNA plasmids, and cell permeant proteins (CPP) have been shown to be effective in reprogramming. mRNA reprogramming has high reprogramming efficiency rate, but method robustness (reproducibility) is low.

DNA-based episomal vector reprogramming was developed to mitigate the issue of vector integration. In this method, somatic cells are transfected with an episomal vector or a set of episomal vectors encoding for reprogramming factors. However, this reprogramming method results in variable reprogramming efficiency and kinetics for the emergence of iPSC colonies, depending on the somatic cell type.

The reprogramming efficiency is further reduced when the cellular reprogramming process is performed in serum-free, animal-free, defined cell culture conditions. The ability to generate iPSCs at sufficient efficiency and in a timely manner, in conditions that are optimized for clinical applications (e.g. utilizing chemically-defined animal component-free cell culture processes), is essential to make iPSCs applicable to therapeutic applications.

Most reprogramming methods rely on ectopic expression of exogenous genes. This ectopic expression induces a series of events which primarily affect the endogenous transcription machinery in the somatic cells. Once iPSC are generated, the expression of the exogenous genes is no longer needed, as the iPSCs should rely on the expression of the endogenous genes to maintain self-renewal and pluripotency. Persistent expression of exogenous reprogramming factors may limit the cell's differentiation potential.

Thus, there is a need for alternative methods for inducing cellular reprogramming in somatic cells, without having to artificially and constitutively express coding sequences of genes that are associated with cell growth and pluripotency.

SUMMARY OF THE INVENTION

The current disclosure provides methods for reprogramming mammalian somatic cells by regulating the expression of endogenous cellular genes. Cellular reprogramming of somatic cells can be induced by activating the transcription of embryonic stem cell-associated genes (e.g., oct3/4) and/or suppressing the transcription of somatic cell-specific and/or cell death-associated genes. The endogenous transcription machinery can be modulated using synthetic transcription factors (activators and suppressors). For example, CRISPR (clustered regularly interspaced palindromic repeats), TALE (transcriptional activator-like effector) or Zinc Finger technologies can be used to modulate the expression of endogenous cellular genes, to allow for faster, and more efficient nuclear reprogramming under conditions amenable for clinical and commercial applications.

In one example, the nuclear reprogramming of somatic cells is accomplished using CRISPR-based technologies.

The CRISPR system was first identified in selected bacterial species and forms part of a prokaryotic adaptive immune system. Short regions of DNA from invading viral or plasmid DNA are captured and integrated into the genome, forming so-called CRISPR arrays, interspaced by repeated sequences from the CRISPR locus. This acquisition of DNA into CRISPR arrays is followed by transcription and RNA processing. Depending on the bacterial species, CRISPR RNA processing proceeds differently. In the type II system (described in the bacterium *Streptococcus pyogenes*) the transcribed RNA is paired with a transactivating RNA (tracrRNA) before being cleaved by RNase III to form an individual CRISPR-RNA (crRNA).

The crRNA is further processed after binding by the Cas9 nuclease to produce the mature crRNA. The crRNA/Cas9 complex subsequently binds to DNA containing complimentary sequences to the captured regions (termed protospacers). The Cas9 protein then cleaves both strands of DNA in a site-specific manner, forming a double strand break (DSB). This provides a DNA-based memory, resulting in rapid degradation of viral or plasmid DNA upon repeat exposure and/or infection. The native CRISPR system has been comprehensively reviewed (see, e.g., Barrangou and Marraffini, Molecular Cell 2014, 54:234-244)

Multiple groups identified potential applications of the CRISPR system in gene editing (Jinek et al., *Science* 2012, 337:816-821; Le Cong et al., *Science* 2013, 339:819-823; Mali et al., *Science* 2013, 339:823-826). This involved utilizing the Cas9 protein in addition to a chimeric RNA designed around individual units from the CRISPR array fused to the tracrRNA. This creates a single RNA species, called the small guide RNA (gRNA) where modification of the sequence in the protospacer region can target the Cas9 protein site-specifically. Considerable work has been done to understand the nature of the base-pairing interaction between the chimeric RNA and the target site, and its tolerance to mismatches, which is highly relevant in order to predict and assess off-target effects (see, e.g., Fu et al., *Nature Biotechnology* 2014, 32(3):279-284, and supporting material).

The CRISPR/Cas9 gene editing system has been used successfully in a wide range of organisms and cell lines, both in order to induce DSB formation with the wild type Cas9 protein or to nick a single DNA strand using a mutant protein termed Cas9n/Cas9 D10A (see, e.g., Mali et al., *Science* 2013, 339:823-826; Sander and Joung, *Nature Biotechnology* 2014, 32(4):347-355). While DSB formation results in creation of small insertions and deletions (indels) which can disrupt gene function, the Cas9n/Cas9 D10A nickase avoids indel creation (repaired by the non-homologous end-joining mechanism) while stimulating the endogenous homologous recombination machinery. The latter mechanism can be used to insert regions of DNA into the genome with high-fidelity.

In relation to other established gene editing technologies such as meganucleases, transcriptional activator-like effector nucleases (TALENs), zinc-finger nucleases (ZFNs) and recombinant adeno-associated viruses (rAAV), CRISPR/Cas9 has a number of advantages, most notably speed and ease of use (see, e.g., Gaj et al., *Trends in Biotechnology* 2013, 31(7):397-405). The fact that targeting is accomplished by an RNA-DNA base pairing interaction, rather than a protein-DNA interaction, makes the system both experimentally simpler and applicable to high throughput applications.

A further development of the CRISPR/Cas9 system is to completely disrupt the nuclease activity of the Cas9 protein and instead use it solely as a DNA targeting mechanism. The defective Cas9 mutant (dCas9) can be fused to functional domains from a variety of proteins, for example, to activate or repress transcription (Sander and Joung 2014). In the same way as the ease of use of this system facilitates gene editing, it also allows rapid generation of CRISPR-transcription factors (CRISPR-TF). Synthetic transcription factors have a multitude of uses including studies of gene function and construction of heterologous transcription units.

Initial attempts to generate CRISPR-TFs utilized genetic fusions of dCas9 to single transactivation or repression domains, along with targeting to regions proximal to the transcription start site (TSS) in the promoter of the gene of interest (Mali et al., *Nature Biotechnology* 2013, 31(9): 833-8). While this proved successful at modulating transcription, large fold-changes in gene expression required use of multiple gRNAs for each target gene. Modulation efficiency can be increased using dual N- and C-terminal fusion of dCas9 to multiple different functional domains, and by using modified gRNAs, which themselves bind the modulating protein. See, e.g., Konermann et al., *Nature* 2015, 517: 583-588 (and supporting material). In the latter case, modulation is achieved using three separate components; the modified gRNA, the RNA binding functional domain protein (for example, MS2-VP64) and the unfused dCas9 protein.

Multiplex gene regulation has also been demonstrated using the CRISPR system. This allows construction of complex regulatory networks and comprehensive interrogation of gene pathway function. It is this aspect in particular which technically distinguishes the CRISPR-based approaches from alternatives. In some examples, iPS cells are generated by activation of certain stem cell-associated genes and concomitant repression of other genes, using synthetic transcription factors, each comprising a transcriptional modulator (activator or suppressor) in combination with specific gRNA(s), which target the transcriptional modulators to the various genes.

In some examples, stem cell-associated genes are activated using synthetic transcriptional activators such as dCas9-VP64 combined with specific gRNA(s) to target the desired genes. Endogenous gene transcription can be suppressed using synthetic transcriptional suppressors, such as dCas9-KRAB combined with specific gRNA(s) to target the desired genes. Alternative transcriptional modulators could also be used, based on CRISPR (see, e.g., Konermann et al., *Nature* 2015, 517: 583-588 (and supporting material); Chavez (2015)) or other synthetic transcription factors (e.g. TALES/ZFs).

In some examples, the synthetic transcription factor elements are introduced into the cell either by transfection with an expression vector (e.g., plasmid vector) encoding the transcriptional modulator (either as a single dCas9 fusion or dCas9 and a separate modulator (e.g. MS2-VP64)) and the gRNA, or by transducing the cells with the mature transcriptional modulator polypeptide/protein(s) and the nucleic acid molecule(s) (gRNA).

While transcription regulation will be artificially induced in the somatic cells, the transcribed genes will have the natural regulatory elements, such as the 5' and 3' UTRs. Likewise, the expression vector (episomal or otherwise) encoding the synthetic transcription factor elements should be diluted with the cell divisions and cleared from the cells by a similar process that leads to vector-free iPSCs where iPSCs are generated by ectopic expression of the reprogramming factors delivered by episomal vectors or Sendai virus.

The direct modulation of endogenous gene transcription can provide one or more of the following advantages: (1) shorten the period of time from somatic cell transfection to iPSC colony appearance (e.g., through the ability to more precisely and/or tightly control expression of the relevant endogenous genes to induce reprogramming); (2) ensure that the newly generated iPSCs rely on their endogenous transcriptional machinery to maintain self-renewal and pluripotency; (3) eliminate the need to verify exogenous gene silencing and/or clearance; (4) minimize the possible 'side-effects' of ectopic expression of coding sequences (i.e. sequences taken outside of their native genomic context), such as silencing and post-transcriptional regulation; and (5) reduce the somatic cell-type dependent variability of reprogramming efficiency.

For example, by turning on/up the initial endogenous genes in a more controlled way, rather than arbitrarily overexpressing reprogramming factors from transiently transfected plasmids, the expression system described herein more closely mimics natural cellular processes.

Method 1

In some aspects, the current disclosure provides methods of nuclear reprogramming of a mammalian somatic cell. The methods include contacting a population of mammalian somatic cells (starting cells) with a synthetic transcription factor, under conditions, and for a period of time sufficient to (a) reprogram the mammalian somatic cell to an induced pluripotent stem cell, or sufficient to (b) transdifferentiate the somatic cell to a target cell substantially different in cell type from the starting cells. In some embodiments, the method further includes culturing the reprogrammed cells to form colonies of iPSCs.

In some embodiments, the above method is an in vitro method. In other examples, the method is an in vivo or ex vivo method.

In some embodiments, the transcription of each candidate gene for transcriptional regulation will be either activated or suppressed by combining sequence-specific gRNAs with CRISPR-based synthetic transcription factors. CRISPR modulation may be combined with other technologies such as small interfering RNAs (siRNAs) to achieve the desired transcriptional output. In some examples, ESC-associated genes are activated. In other examples, genes associated with apoptotic induction are suppressed. In yet other examples, the before mentioned strategies are used simultaneously, i.e., ESC-associated genes are activated, and genes associated with apoptotic induction are suppressed.

In some embodiments of the above methods, the synthetic transcription factor comprises (a) at least one guide RNA (gRNA) comprising a DNA-binding segment and a polypeptide-binding segment, wherein the DNA-binding segment binds the promoter region of a pluripotency factor gene, e.g., (i) an embryonic stem cell (ESC)-associated gene, or (ii) a gene associated with apoptotic induction; and (b) at least one transcriptional modulator (e.g., dCas9-VP64), which binds the polypeptide-binding segment of the guide RNA.

In other embodiments, the synthetic transcription factor does not include a guide RNA, but incorporates a DNA-binding domain capable of binding directly to the regulatory DNA sequences of the target gene, e.g., (i) the promoter region of an embryonic stem cell (ESC)-associated gene (e.g., oct3/4), or (ii) the promoter region of a gene associated with apoptotic induction (e.g., p53).

In some examples, according to any of the above embodiments, the endogenous pluripotency factor gene being activated is a reprogramming factor gene or a combination of at least two reprogramming factor genes. Exemplary reprogramming factor genes include POU5F1 (oct3/4), sox2, klf4, c-myc, lin28, and nanog.

In other examples according to any of the above embodiments, the pluripotency factor gene being activated is an anti-apoptotic gene, for example bcl-2 or bcl-x. In some examples, the reprogramming factor genes being activated are at least two of oct3/4, sox-2, klf-4, c-myc, lin28, and nanog, and at least one anti-apoptotic gene (e.g., at least one of bcl-2 and bcl-x).

In further examples according to any of the above embodiments, cellular reprogramming involves repression of at least one target gene, e.g., in combination with any one of the above described gene activations. In some examples, the pluripotency factor gene being repressed is selected from p53, p21, p19$^{Arf}$, and p16$^{Ink4a}$.

In other examples according to any of the above embodiments, the pluripotency factor gene being repressed is a gene encoding for signal transduction proteins that promote cell death and/or cell cycle arrest. In some examples, the target gene being repressed is selected from ROCK, a PKA/PKG/PKC family kinase, and other genes that when repressed would inhibit the mTOR pathway.

In other examples according to any of the above embodiments, the pluripotency factor gene(s) being repressed or activated are involved in affecting the epigenetic state of the cell in order that chromatin is in a transcriptionally competent state when targeted by the synthetic transcription factor(s)

Another pluripotency factor gene useful in the methods of the invention is glis1.

In some examples, reprogramming is induced using transcriptional activation of at least two reprogramming factor genes (e.g., oct3/4 and sox2). In other examples, reprogramming is induced using activation of at least three reprogramming factor genes (e.g., oct3/4, sox2, and klf4). In yet other examples, reprogramming is induced using activation of at least four reprogramming factor genes (e.g., oct3/4, sox2, c-myc, and klf4).

In other examples according to Method 1, the population of mammalian somatic cells is contacted with at least two synthetic transcription factors, each targeting a different gene.

Method 2

In other aspects, the present disclosure provides in vitro screening methods for identifying candidate pluripotency factor genes.

For example, somatic cells are transfected with a CRISPR based transcriptional activator and a library of candidate gRNAs, along with an episomal vector mix lacking at least one of the reprogramming factor genes, otherwise necessary for iPSC formation. Transfecting cells with the episomal mix lacking at least one of the reprogramming factor genes alone should results in 0% or very low reprogramming efficiency. Achieving reprogramming after addition of the Cas9-based activator and the gRNA library indicates that at least one gene participating in the reprogramming process was activated, and activation of that gene was able to compensate for the missing reprogramming factor.

An exemplary screening method includes (a) contacting a population of mammalian somatic cells with: (i) at least one candidate gRNA comprising a DNA-binding segment and polypeptide-binding segment(s); and (ii) a synthetic transcriptional modulator (either composed of single or multiple proteins), which binds the polypeptide-binding segment(s) of the candidate gRNA, for a period of time, and under conditions sufficient to reprogram the mammalian somatic cells to induced pluripotent stem cells (iPSCs), thereby forming a population of test cells. In one embodiment, the method further includes (b) culturing the test cells, e.g., for a period of time and under conditions sufficient to form iPS cell colonies.

In some embodiments according to Method 2, successful reprogramming is indicated by the formation of one or more iPSC colonies upon culturing of the test cell population. In other embodiments, formation of at least one iPSC colony indicates that the candidate gRNA/transcriptional activator complex hybridized (i.e., bound) to the promoter region of a pluripotency factor gene, which was subsequently expressed in its host cell, thereby contributing to the nuclear reprogramming of the host cell.

In some embodiments according to Method 2, the population of somatic cells is contacted with a library of candidate gRNAs representing a variety of different DNA-binding segments.

In some examples according to any of the embodiments of Method 1 and 2, the methods further include measuring reprogramming efficiency.

In some examples according to any of the above embodiments, the transcriptional modulator includes an RNA-binding domain and a functional domain selected from a transcriptional activation domain (e.g., VP64 or p65) and a transcriptional suppressor domain (e.g., KRAB).

In some examples, the dCas9 polypeptide is fused to a transcriptional activation domain (e.g., VP64 or p65). In other examples, the dCas9 polypeptide is fused to a transcriptional repressor domain (e.g., KRAB).

In other examples according to any of the above embodiments, the methods further include contacting the population of mammalian somatic cells with at least one expression vector encoding for the synthetic transcription factor components. Thus, the components of the synthetic transcription factor (e.g., dCas9-VP64 and gRNA) are cloned into appropriate expression vectors. Cellular reprogramming will be induced in somatic cells upon transfecting the target cells with at least one expression vector encoding for the synthetic transcription factor(s).

In some examples, the expression vector encoding for the synthetic transcription factor(s) is an episomal vector (i.e., a plasmid vector).

In one example, the components of the synthetic transcription factor are cloned into a single expression vector. For example, the population of mammalian somatic cells is contacted with an expression vector encoding at least one guide RNA and at least one transcriptional modulator (e.g., dCas9-VP64). In other examples according to any of the above embodiments, the methods further include contacting the population of mammalian somatic cells with at least two expression vectors encoding for the synthetic transcription factor components. In some examples, the components of a synthetic transcription factor are cloned into separate vectors. For example, the population of mammalian somatic cells is contacted with a first expression vector encoding at least one guide RNA, and a second expression vector encoding at least one transcriptional modulator (e.g., dCas9-VP64).

In some examples according to any of the above embodiments, the transcriptional modulator is provided to the cell as a polypeptide/protein (e.g., dCas9-VP64 polypeptide). Accordingly, the methods include contacting the population of mammalian somatic cells with at least one synthetic transcriptional modulator polypeptide. Methods for introducing or facilitating entry of polypeptides into a somatic cell are known to those of skill in the art.

In some embodiments, a transcriptional modulator polypeptide will comprise a polypeptide permeant domain. A number of permeant domains, such as polypeptides, peptidomimetics, and non-peptide carriers, are known in the art and may be used in the in the present invention. For example, a permeant polypeptide may be derived from the third alpha helix of Drosophila melanogaster transcription factor Antennapaedia, referred to as penetratin.

In other examples, the guide RNA is provided to the cell as an isolated nucleic acid molecule. Accordingly, the methods of the current disclosure can include contacting the population of mammalian somatic cells with at least one isolated gRNA (nucleic acid).

In other examples, according to any of the above embodiments, the synthetic transcription factor is provided to the somatic cell as a polypeptide (e.g., dCas9-VP64 polypeptide), and the guide RNA is provided to the cell as a nucleic acid molecule. Accordingly, the methods of the current disclosure include contacting the population of mammalian somatic cells with at least one gRNA (nucleic acid), and at least one transcriptional modulator polypeptide.

In some embodiments, the population of somatic cells is further contacted with at least one exogenous reprogramming factor. The exogenous reprogramming factor can be introduced into the cell using an expression vector (e.g., an episomal vector) encoding the exogenous reprogramming factor, or can be introduced into the target cells as a polypeptide, e.g., a recombinant protein. In some embodiments, the reprogramming factors are provided as cell permeant proteins. In a further embodiment, the exogenous reprogramming factors are provided as nucleic acids encoding reprogramming proteins. In some examples, the exogenous reprogramming factor is selected from Oct3/4, Sox2, Klf-4, c-Myc, Lin28, Nanog, SV40 large T-antigen, and combinations thereof. In other examples, the exogenous reprogramming factor is selected from Sox2, Klf-4, c-Myc, SV40 large T-antigen, and combinations thereof. In other examples, the exogenous reprogramming factor is selected from Sox2, Lin28, Nanog, and combinations thereof.

In other embodiments, reprogramming of a somatic cell and formation of iPS cells is accomplished using only activation/repression of endogenous genes as described herein, and does not involve introducing exogenous reprogramming factor genes into the somatic cell. In some examples, the reprogramming methods include repressing the expression of at least one gene in the somatic cell. Typically, the methods will include activating the expression of at least two, at least three, or at least four reprogramming factor genes, and will further include repressing the expression of at least one gene, for example a gene involved in cellular apoptosis (e.g., p53, p21, or a ROCK pathway gene).

In some examples according to any of the above embodiments, the mammalian somatic cells are human cells. In other examples according to any of the above embodiments, the mammalian somatic cells are primary cells (i.e., isolated from a mammalian subject). The primary cells may be cultured for a limited number of passages, e.g., one or two passages, before being cryopreserved. In still other examples, the mammalian somatic cells are blood cells (e.g., peripheral blood mononuclear cells (PBMCs), cord blood mononuclear cells), or fibroblasts. In some examples, the mammalian somatic cells are human primary cells. In other examples, the mammalian somatic cells are primary human PBMCs, primary human cord blood mononuclear cells, or primary human fibroblasts. In other examples, the mammalian somatic cells are not cell lines. For example, the cells being reprogrammed according to the methods described herein are not HEK 293 T cells.

Other aspects of the current disclosure relate to a population of induced pluripotent stem cells produced by any of the methods of the disclosure. In some embodiments, the induced pluripotent stem cells are human cells. In other embodiments, the iPSCs are substantially free of expression vector components. Absence or presence of expression vector components may be determined using any art recognized method, e.g., PCR methods utilizing vector specific primer sequences.

In yet other aspects, the current disclosure provides pharmaceutical compositions containing the iPSCs of the current disclosure along with a pharmaceutically acceptable carrier.

In further aspects, the current disclosure provides methods of treating a disease, e.g., a disease amenable to stem cell therapy, in a patient. The methods include administering to a patient in need thereof a therapeutically effective amount of a pharmaceutical composition according to the present disclosure.

In yet other aspects, the present disclosure provides a composition containing a population of human primary cells, at least one isolated guide RNA of the present disclosure, and at least one transcriptional modulator polypeptide of the present disclosure (e.g., dCas9-VP64), wherein the transcriptional modulator is capable of binding the guide RNA. The composition may further include an exogenous reprogramming factor.

In further aspects, the present disclosure provides a kit for practicing the methods disclosed herein.

DETAILED DESCRIPTION OF THE INVENTION

Figure 1:
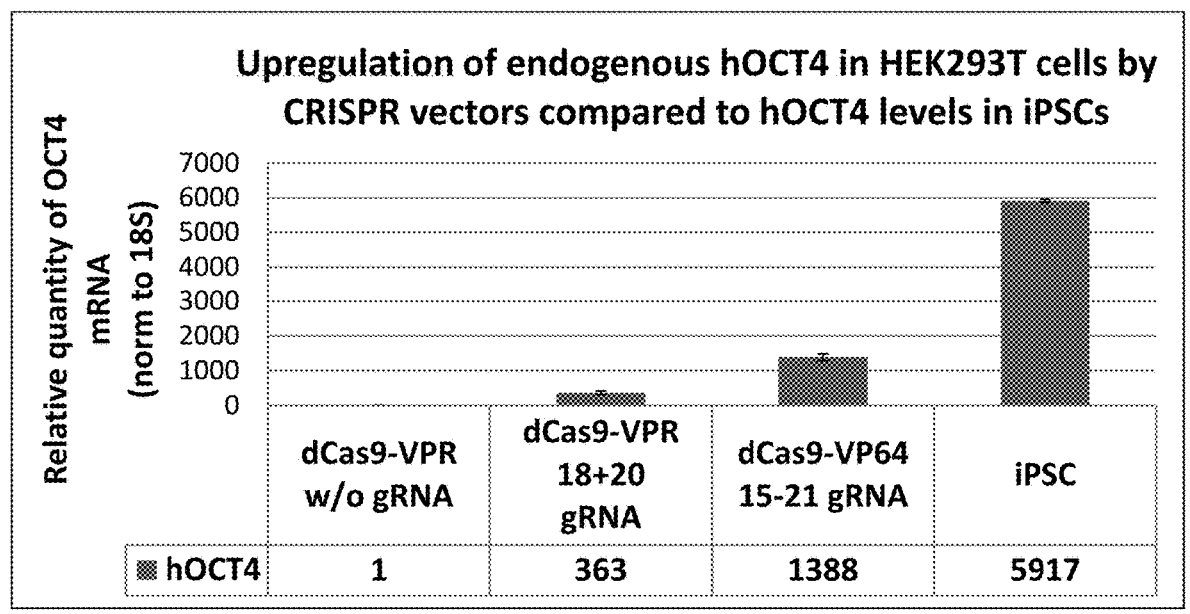
FIG. 1. Upregulation of endogenous hOCT4 in HEK293T cells by CRISPR vectors compared to hOCT4 levels in iPSCs. Relative mRNA expression levels were measured by qRT-PCR 48 hours post transfection. Transfection with dCas9-VPR vector w/o gRNAs was used as baseline. Data represent mean±stdv, n=3 independent transfections.

Described herein are methods of nuclear reprogramming mammalian somatic cells using synthetic transcription factors, e.g., by modulating endogenous reprogramming factor/pluripotency genes. Exemplary methods include contacting a population of mammalian somatic cells (starting somatic cells) with a synthetic transcription factor or a set of synthetic transcription factors, under conditions, and for a period of time sufficient to reprogram the mammalian somatic cell to an induced pluripotent stem cell. Alternatively, conditions are selected that are sufficient to transdifferentiate the somatic cell to a target cell substantially different in cell type from the starting somatic cell. For example, a blood cell may be transdifferentiated into a neuronal cell.

The methods may involve one or more synthetic transcription factors designed to target a particular gene of interest.

In some embodiments, the synthetic transcription factor does not include a separate gRNA, but includes a DNA-binding domain, which is capable of binding directly to a regulatory DNA sequence, e.g., the promoter sequence of a pluripotency factor gene, e.g., an embryonic stem cell (ESC)-associated gene, or a gene associated with the induction of apoptosis.

In other embodiments, a synthetic transcription factor includes at least one (DNA-binding) guide RNA molecule and an RNA-binding polypeptide that includes a functional or regulatory domain. For example, each synthetic transcription factor includes (a) at least one guide RNA comprising a DNA-binding segment and a polypeptide-binding segment, wherein the DNA-binding segment is sequence specific and specifically binds, e.g., the promoter region of a pluripotency/reprogramming factor gene, e.g., an embryonic stem cell (ESC)-associated gene, or a gene associated with the induction of apoptosis. The synthetic transcription factor further includes at least one transcriptional modulator factor, which binds the polypeptide-binding segment of the guide RNA. Based on the interaction between the guide RNA and the synthetic transcription factor, the transcription factor, which includes a functional domain (e.g., a transcriptional activation domain), is targeted to a specific gene of interest, a DNA location within the cellular genome (e.g., the promoter region of an endogenous reprogramming factor gene). Subsequently, the recruitment of the transcriptional modulator to the regulatory gene sequences modulates expression of the endogenous gene of interest, e.g., driving the expression of a pluripotency gene, thereby contributing to the reprogramming of the cell. Using multiple synthetic transcription factors, the expression of multiple pluripotency factor genes can be modulated.

In some embodiments, the method further includes culturing the reprogrammed cells. In some embodiments, reprogrammed cells are cultured for a sufficient amount of time, or a sufficient number of cell doublings to form iPSCs substantially free of expression vector components.

Accordingly, this disclosure describes methods of nuclear reprogramming as well as cells obtained from such methods along with therapeutic methods for using such cells for the treatment of diseases amendable to treatment by stem cell therapy as well as kits for such uses.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

Definitions

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the method/device being employed to determine the value, or the variation that exists among the study subjects. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the current disclosure, and vice versa. Furthermore, compositions of the current disclosure can be used to achieve methods of the current disclosure.

By "somatic cell" it is meant any cell in an organism that has differentiated sufficiently, so that in the absence of experimental manipulation, does not ordinarily give rise to cells of all three germ layers of the body, i.e., ectoderm, mesoderm and endoderm. "Somatic cell" includes "multipotent cells" (i.e., progenitor cells), but does not include "pluripotent" or "totipotent cells." For example, somatic cells would include both neurons and neural progenitors, the latter of which may be able to naturally give rise to all or some cell types of the central nervous system but cannot give rise to cells of the mesoderm or endoderm lineages.

"Multipotency" is referred to herein in the context of multipotent progenitor cells which have the potential to give rise to multiple cell types, but are less potent (more limited in their differentiation potential) than a pluripotent stem cell. For example, a multipotent stem cell is a hematopoietic cell that can develop into several types of blood cells, but cannot develop into brain cells or other types of cells.

"Pluripotent" is referred to herein as the property of a cell/cell type as having the potential to differentiate into any of the three germ layers: endoderm (e.g., interior stomach lining, gastrointestinal tract, the lungs), mesoderm (e.g., muscle, bone, blood, urogenital), or ectoderm (e.g., epidermal tissues and nervous system).

"Pluripotent stem cells" include natural pluripotent stem cells and induced pluripotent stem cells. They can give rise to any fetal or adult cell type. However, alone they generally cannot develop into a fetal or adult organism because they lack the potential to contribute to extra-embryonic tissue, such as the placenta.

"Induced pluripotent stem cells" or ("iPSCs") are similar to natural pluripotent stem cells, such as embryonic stem cells, in many aspects, such as the expression of certain stem cell genes and/or proteins, chromatin methylation patterns, doubling time, embryoid body formation, teratoma formation, viable chimera formation, and potency and differentiability. Induced pluripotent cells may be derived from for example, adult stomach, liver, skin cells and blood cells (e.g., cord blood cells). iPSCs may be derived by transfection of synthetic transcription factors and/or certain stem cell-associated genes into non-pluripotent (e.g., somatic) cells. In certain embodiments, transfection may be achieved through viral vectors, such as retroviruses, for example, and non-viral or episomal vectors. Transfected genes can include, but are not limited to, reprogramming factors Oct3/4 (Pou5f1), Klf-4, c-Myc, Sox-2, Nanog and Lin28. Sub-populations of transfected cells may begin to become morphologically and biochemically similar to pluripotent stem cells, and can be isolated through morphological selection, doubling time, or through a reporter gene and antibiotic selection.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" or "interaction" as used herein (e.g. with reference to a synthetic transcriptional modulator binding the polypeptide-binding segment of a guide RNA) refers to a non-covalent interaction between macromolecules (e.g., between DNA and RNA, or between a polypeptide and a polynucleotide). "Binding" may also be referred to as "associated with" or "interacting". "Binding" as used herein means that the binding partners are capable of binding to each other (e.g., will not necessarily bind to each other). Some portions of a binding interaction may be sequence-specific, but not all components of a binding interaction need be sequence-specific (e.g., contacts with phosphate residues in a DNA backbone). Binding interactions are generally characterized by a dissociation constant (Kd), e.g., less than 1 mM, less than 100 uM, less than 10 uM, less than 1 uM, less than 100 nM, less than 10 nM. "Affinity" refers to the strength of binding, increased binding affinity being correlated with a lower Kd.

As used herein, "promoter," "promoter sequence," or promoter region" refers to a DNA regulatory region/sequence capable of binding RNA polymerase and involved in initiating transcription of a downstream coding or non-coding sequence. In some examples of the present disclosure, the promoter sequence includes the transcription initiation site and extends upstream to include the minimum number of bases or elements necessary to initiate transcription at levels detectable above background. In some embodiments, the promoter sequence includes a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the various vectors of the present invention.

A "vector" or "expression vector" is a replicon, such as a plasmid, phage, virus, or cosmid, to which another DNA segment, i.e. an "insert", may be attached so as to bring about the replication of the attached DNA segment in a cell. "Vector" includes episomal (e.g., plasmids) and non episomal vectors. In some embodiments of the present disclosure the vector is an episomal vector, which is removed/lost from a population of cells after a number of cellular generations, e.g., by asymmetric partitioning.

An "expression cassette" comprises a DNA coding sequence operably linked to a promoter. "Operably linked" refers to a juxtaposition wherein the components so described are in a relationship permitting them to function in their intended manner. For instance, a promoter is operably linked to a coding sequence if the promoter affects its transcription or expression.

The terms "recombinant expression vector," or "DNA construct" are used interchangeably herein to refer to a DNA molecule comprising a vector and at least one insert. Recombinant expression vectors are usually generated for the purpose of expressing and/or propagating the insert(s), or for the construction of other recombinant nucleotide sequences. The insert(s) may or may not be operably linked to a promoter sequence and may or may not be operably linked to DNA regulatory sequences.

The term "efficiency of reprogramming" or "reprogramming efficiency" may be used to refer to the ability of cells to give rise to iPS cell colonies, e.g., when contacted with the synthetic transcription factors of the current disclosure. Somatic cells that demonstrate an enhanced efficiency of reprogramming to pluripotency will demonstrate an enhanced ability to give rise to iPSCs relative to a control. The term "efficiency of reprogramming" may also refer to the ability of somatic cells to be reprogrammed to a substantially different somatic cell type, a process known as transdifferentiation. The efficiency of reprogramming using the methods of the current disclosure vary with the particular combination of somatic cells, method of introducing synthetic transcription factors or reprogramming factors, and culturing methods following induction of reprogramming. The methods of the current disclosure may include "measuring reprogramming efficiency." Determining the reprogramming efficiency can involve counting iPSC colonies, or may include measuring the expression of pluripotency markers, such as the below "key pluripotency markers" by the reprogrammed cells.

"Key pluripotency markers" known by one of ordinary skill in the art include but are not limited to the gene and/or protein expression of alkaline phosphatase, SSEA3, SSEA4, Sox2, Oct3/4, Nanog, TRA160, TRA181, TDGF 1, Dnmt3b, FoxD3, GDF3, Cyp26a1, TERT, and zfp42.

"Treating" or "treatment" is referred to herein as administration of a substance (e.g., pharmaceutical composition of the present disclosure) to a subject with the purpose to cure, alleviate, relieve, remedy, prevent, or ameliorate a disease or disorder, symptoms of the disorder, a disease state secondary to the disorder, or predisposition toward the disorder. An "effective amount" is an amount of the substance that is capable of producing a medically desirable result as delineated herein in a treated subject. The medically desirable result may be objective (i.e., measurable by some test or marker) or subjective (i.e., subject gives an indication of or feels an effect).

"Disease amenable to treatment with stem cell therapy" as referred to herein means any procedures, conditions, disorders, ailments and/or illnesses which can be treated by the administration of stem cells such as iPSCs. Such diseases include but are not limited to bone marrow, skin, heart, and corneal transplantation, graft versus host disease, hepatic and renal failure, lung injury, rheumatoid arthritis, treatment of autoimmune diseases such as Crohn's disease, ulcerative colitis, multiple sclerosis, lupus and diabetes; prevention of allograft rejection, neurological disorders and cardiovascular medicine; as well as Acute lymphoblastic leukemia (ALL), Acute myeloid leukemia (AML), Burkitt's lymphoma, Chronic myeloid leukemia (CIVIL), Juvenile myelomonocytic leukemia (JMML), Non-Hodgkin's lymphoma Hodgkin's lymphoma, Lymphomatoid granulomatosis, Myelodysplastic syndrome (MDS), Chronic myelomonocytic leukemia (CMML), Bone Marrow Failure Syndromes, Amegakaryocytic thrombocytopenia, Autoimmune neutropenia (severe), Congenital dyserythropoietic anemia, Cyclic neutropenia, Diamond-Blackfan anemia, Evan's syndrome, Fanconi anemia, Glanzmann's disease, Juvenile dermatomyositis, Kostmann's syndrome, Red cell aplasia, Schwachman syndrome, Severe aplastic anemia, Congenital sideroblastic anemia, Thrombocytopenia with absent radius (TAR syndrome), Dyskeratosis congenital, Blood Disorders, Sickle-cell anemia (hemoglobin SS), HbSC disease, Sickle βo Thalassemia, α-thalassemia major (hydrops fetalis), β-thalassemia major (Cooley's anemia), β-thalassemia intermedia, E-βo thalassemia, E-β+ thalassemia, Metabolic Disorders, Adrenoleukodystrophy Gaucher's disease (infantile), Metachromatic leukodystrophy, Krabbe disease (globoid cell leukodystrophy), Gunther disease, Hermansky-Pudlak syndrome, Hurler syndrome, Hurler-Scheie syndrome, Hunter syndrome, Sanfilippo syndrome, Maroteaux-Lamy syndrome, Mucolipidosis Type II, III, Alpha mannosidosis, Niemann Pick Syndrome, type A and B, Sandhoff Syndrome, Tay-Sachs Disease, Batten disease (inherited neuronal ceroid lipofuscinosis), Lesch-Nyhan disease, Immunodeficiencies, Ataxia telangiectasia, Chronic granulomatous disease, DiGeorge syndrome, IKK gamma deficiency, Immune dysregulation polyendocrineopathy, X-linked Mucolipidosis, Type II, Myelokathexis X-linked immunodeficiency, Severe combined immunodeficiency, Adenosine deaminase deficiency, Wiskott-Aldrich syndrome, X-linked agammaglobulinemia, X-linked lymphoproliferative disease, Omenn's syndrome, Reticular dysplasia, Thymic dysplasia, Leukocyte adhesion deficiency, Other Osteopetrosis, Langerhans cell histiocytosis, Hemophagocytic lymphohistiocytosis, Acute & Chronic Kidney Disease, Alzheimer's disease, Anti-Aging, Arthritis, Asthma, Cardiac Stem Cell Therapy, Cerebral Infarction (Stroke), Cerebral Palsy (Stroke), Chronic Obstructive Pulmonary Disease (COPD), Congestive Heart Failure, Diabetes Mellitus (Type I & II), Fibromyalgia, Immune Deficiencies, Ischemic Heart Disease, Lupus, Multiple Sclerosis, Myocardial Infarction, Osteoarthritis, Osteoporosis, Parkinson's Disease, Peripheral Arterial Disease, Rheumatoid Arthritis, Stem Cell Therapy in Plastic Surgery, Traumatic Brain Injury and Neurological Diseases.

"Patient" as used herein refers to a mammalian subject diagnosed with or suspected of having or developing a disease amenable to stem cell therapy, e.g., cardiovascular disease. Exemplary patients may be humans, apes, dogs, pigs, cattle, cats, horses, goats, sheep, rodents and other mammals that can benefit from stem cell therapies.

"Administering" is referred to herein as providing the iPSCs of the current disclosure to a patient, e.g., by injection. By way of example and not limitation, administration may be performed by intravenous (i.v.) injection, subcutaneous (s.c.) injection, intradermal (i.d.) injection, intraperitoneal (i.p.) injection, or intramuscular (i.m.) injection. One or more such routes may be employed. Parenteral administration can be, for example, by bolus injection or by gradual perfusion over time. Alternatively, or concurrently, administration may be by the oral route. Additionally, administration may also be by surgical deposition of a bolus or pellet of cells, or positioning of a medical device, e.g., a stent, loaded with cells. Preferably, the compositions of the invention are administered at the site of disease, e.g. at the site or near (e.g., about or at least 1, 2, 3, 4, 5, 6, 7, 8, 9, 10, 11, 12, 13, 14, 15, 16, 17, 18, 19, 20, 25, 30, 40, 50 millimeters from) the site of a disease lesion (e.g., vascular stenosis/blockage, necrotic tissue or site of gangrenous infection).

"A patient in need thereof" is referred to herein as a patient diagnosed with or suspected of having a disease amendable to stem cell therapy.

Pluripotency Factors and Pluripotency Factor Genes

The term "pluripotency factor gene" or "reprogramming factor gene" as used herein means an endogenous cellular gene encoding a pluripotency factor polypeptide (including its promoter region). Activation or repression of the expression of a pluripotency factor gene contributes to the nuclear reprogramming of a somatic cell, e.g., to multipotency or pluripotency. "Pluripotency factor gene" includes any target gene useful in the methods of the invention. Exemplary pluripotency factor genes include ESC-associated genes, such as reprogramming factor genes (which are typically activated in the methods of the present disclosure), and genes involved in initiating apoptosis (which are typically suppressed in the methods of the present disclosure).

"Pluripotency factor" or "reprogramming factor," as used herein, refers to the corresponding gene product of the above "pluripotency factor gene" or "reprogramming factor gene."

The term "candidate pluripotency factor gene" refers to a gene potentially involved in nuclear reprogramming of a mammalian somatic cell, which is identified using the in vitro screening methods of the current disclosure utilizing candidate guide RNA (e.g., a library of candidate guide RNAs). Activation or repression of the expression of such gene results in the formation of iPSCs, e.g., the formation of at least one iPSC colony when undergoing an appropriate reprogramming procedure as outlined herein. The formation of an iPSC can indicate that a candidate guide RNA has hybridized to the promoter region of the candidate gene, and has targeted a transcriptional modulator to the regulatory region of the candidate gene. Subsequently, expression of the candidate gene has been modulated, thus potentially contributing to the reprogramming of the host cell. Identification of the "candidate pluripotency factor gene" may further involve matching the DNA-binding sequence of the candidate guide RNA with an endogenous gene sequence. Involvement of the candidate gene in reprogramming can be further verified, e.g., by repeating reprogramming of mammalian somatic cells using additional candidate gRNAs having the identified DNA-binding segment in combination with one or more transcriptional modulators of the present disclosure.

Exemplary reprogramming factor genes include POU5F1 (oct3/4), sox2, klf4, c-myc, lin28, and nanog. In some examples, the reprogramming factor genes being activated are at least two of oct3/4, sox-2, klf-4, c-myc, lin28, and nanog. In some examples, the reprogramming factor genes being activated are at least two of oct3/4, sox2, lin28, and nanog. In still other examples, the reprogramming factor genes are at least two of oct3/4, sox2, c-myc, and klf4. In other examples, the reprogramming factor genes being activated are at least three of oct3/4, sox2, lin28, and nanog. In still other examples, the reprogramming factor genes are at least three of oct3/4, sox2, c-myc, and klf4. In some examples, the reprogramming factor genes being activated are oct3/4, sox2, lin28, and nanog. In still other examples, the reprogramming factor genes being activated are oct3/4, sox-2, c-myc, and klf4.

In other examples according to any of the above embodiments, the gene being activated is an anti-apoptotic gene, for example bcl-2 or bcl-x. In some examples, the reprogramming factor genes being activated are at least two of oct3/4, sox-2, klf-4, c-myc, lin28, and nanog, and at least one anti-apoptotic gene (e.g., at least one of bcl-2 and bcl-x). In other examples, the reprogramming factor genes being activated are at least two of oct3/4, sox2, lin28, and nanog, and at least one anti-apoptotic gene (e.g., at least one of bcl-2 and bcl-x). In still other examples, the reprogramming factor genes being activated are at least two of oct3/4, sox2, c-myc, and klf4, and at least one anti-apoptotic gene (e.g., at least one of bcl-2 and bcl-x). In some examples, the reprogramming factor genes being activated are at least three of oct3/4, sox-2, lin28, and nanog, and at least one anti-apoptotic gene (e.g., at least one of bcl-2 and bcl-x). In still other examples, the reprogramming factor genes are at least three of oct3/4, sox2, c-myc, and klf4, and at least one anti-apoptotic gene (e.g., at least one of bcl-2 and bcl-x). In some examples, the reprogramming factor genes being activated are oct3/4, sox2, lin28, and nanog, and at least one anti-apoptotic gene (e.g., at least one of bcl-2 and bcl-x). In still other examples, the reprogramming factor genes being activated are oct3/4, sox-2, c-myc, and klf4, and at least one anti-apoptotic gene (e.g., at least one of bcl-2 and bcl-x).

Cellular reprogramming is traditionally accomplished using a combination of transcription factors (e.g., Oct3/4, Sox2, Klf4, Nanog, c-Myc and Lin28), as well as genes that encode for proteins functioning as apoptotic repressors. Examples for these genes are SV-40 Large T-Antigen and the dominant negative form of the tumor suppressor protein, p53. Because genes for these apoptotic repressors do not reside endogenously in the human cell genome, in the CRIPR approach, apoptotic pathways that might be activated during the process of cellular reprogramming should be suppressed.

Thus, in further examples according to any of the above embodiments, cellular reprogramming involves repression of at least one target gene, e.g., in combination with any one of the above described gene activations. In some examples, the target gene being repressed is an apoptosis promoting gene or a cell cycle inhibitor. Examples include p53 and its target gene p21, a cell cycle inhibitor. Repressing other cell cycle inhibitors could counteract apoptosis pathways triggered by the cellular reprogramming process. Some candidates are $p19^{Arf}$ (which stabilizes p53) and $p16^{Ink4a}$ (which prevents pRb from being phosphorylated by Cyclin D, and therefore induces cell cycle arrest). The Ink4/Arf locus is epigenetically silenced in iPSC, but upregulated in somatic cells, suggesting an important role of the Ink4a/Arf locus as an epigenetic barrier to reprogramming (H. Li, M. Collado, A. Villasante et al., "The Ink4/Arf locus is a barrier for iPS cell reprogramming," *Nature* 2009, 460(7259): 1136-1139). Thus, in some examples, the target gene being repressed is selected from p53, p21, $p19^{Arf}$, and $p16^{Ink4a}$.

In other examples according to any of the above embodiments, the pluripotency factor gene being repressed is a gene encoding for signal transduction proteins that promote cell death and/or cell cycle arrest. Examples include Rho-associated protein kinase (ROCK), and kinases belonging to the AGC (PKA/PKG/PKC) family of serine-threonine kinases. ROCK is mainly involved in regulating the shape and movement of cells by acting on the cytoskeleton. ROCK inhibition has been shown to promote cell survival of pluripotent stem cells as single cells, by preventing dissociation-induced apoptosis. Moreover, repressing ROCK will potentially inhibit the mTOR pathway. Inhibition of the mTOR pathway by rapamycin, for example, notably enhances the reprogramming efficiency (T. Chen, L. Shen, J. Yu et al., "Rapamycin and other longevity promoting compounds enhance the generation of mouse induced pluripotent stem cells," *Aging Cell* 2011, 10(5):908-911). Thus, in some examples, the pluripotency factor gene being repressed is selected from ROCK, a PKA/PKG/PKC family kinase, and other genes who's repression would inhibit the mTOR pathway.

Another pluripotency factor gene useful in the methods of the invention is glis1.

Reprogramming factors of interest also include factors useful in transdifferentiation, where a somatic cell is reprogrammed to a different somatic cell. For the purpose of transdifferentiation of one somatic cell to another, substantially different, somatic cell type, a different set of reprogramming factors finds use. For example, to transdifferentiate a fibroblast to a cardiomyocyte, one might use cell permeant peptides Gata4, Mef2c and Tbx5 (Leda et al., Cell 2010, 142(3): 375-386, herein specifically incorporated by reference.)

In some embodiments of the present disclosure, mammalian somatic cells are contacted with an exogenous reprogramming factor. Exogenous reprogramming factors are provided to the cell as compositions of isolated polypeptides, i.e. in a biologically active cell-free form, or as exogenous nucleic acids (e.g., DNA, RNA) encoding the same, which upon delivery to the cell or upon expression, reprogram or contribute to reprogramming a somatic cell to, e.g., multipotency or pluripotency. In some embodiments, the reprogramming factors may be non-integrating, i.e., provided to the recipient somatic cell in a form that does not result in integration of exogenous DNA into the genome of the recipient cell.

Biological activity may be determined by specific DNA binding assays; or by determining the effectiveness of the factor in altering cellular transcription. A composition of the invention may provide one or more biologically active reprogramming factors. The composition may comprise at least about 50 µg/ml soluble reprogramming factor, at least about 100 µg/ml; at least about 150 µg/ml, at least about 200 µg/ml, at least about 250 µg/ml, at least about 300 µg/ml, or at least about 500 ug/ml.

A Klf4 polypeptide is a polypeptide comprising the amino acid sequence that is at least 70% identical to the amino acid sequence of human Klf4, i.e., Kruppel-Like Factor 4 the sequence of which may be found at GenBank Accession Nos. NP_004226 (SEQ ID NO: 1) and NM_004235 (SEQ ID NO: 2). Klf4 polypeptides, e.g. those that are at least 70%, 75%, 80%, 85%, 90%, 91%, 92%, 95%, 97%, 99%, or 100% identical to the sequence provided in GenBank Accession No. NM_004235 (SEQ ID NO: 2), and the nucleic acids that encode them find use as a reprogramming factor in the present invention.

A c-Myc polypeptide is a polypeptide comprising an amino acid sequence that is at least 70% identical to the amino acid sequence of human c-Myc, i.e., myelocytomatosis viral oncogene homolog, the sequence of which may be found at GenBank Accession Nos. NP_002458 (SEQ ID NO: 3) and NM_002467 (SEQ ID NO: 4). c-Myc polypeptides, e.g. those that are at least 70%, 75%, 80%, 85%, 90%, 91%, 92%, 95%, 97%, 99%, or 100% identical to the sequence provided in GenBank Accession No. NM_002467 (SEQ ID NO: 4), and the nucleic acids that encode them find use as a reprogramming factor in the present invention.

A Nanog polypeptide is a polypeptide comprising an amino acid sequence that is at least 70% identical to the amino acid sequence of human Nanog, i.e., Nanog homeobox, the sequence of which may be found at GenBank Accession Nos. NP_079141 (SEQ ID NO: 5) and NM 024865 (SEQ ID NO: 6). Nanog polypeptides, e.g. those that are at least 70%, 75%, 80%, 85%, 90%, 91%, 92%, 95%, 97%, 99%, or 100% identical to the sequence provided in GenBank Accession No. NM_024865 (SEQ ID NO: 6), and the nucleic acids that encode them find use as a reprogramming factor in the present invention.

A Lin-28 polypeptide is a polypeptide comprising an amino acid sequence that is at least 70% identical to the amino acid sequence of human Lin-28, i.e., Lin-28 homolog of C. elegans, the sequence of which may be found at GenBank Accession Nos. NP_078950 (SEQ ID NO: 7) and NM_024674 (SEQ ID NO: 8). Lin-28 polypeptides, e.g. those that are at least 70%, 75%, 80%, 85%, 90%, 91%, 92%, 95%, 97%, 99%, or 100% identical to the sequence provided in GenBank Accession No. NM_024674 (SEQ ID NO: 8), and the nucleic acids that encode them find use as a reprogramming factor in the present invention.

An Oct3/4 polypeptide is a polypeptide comprising an amino acid sequence that is at least 70% identical to the amino acid sequence of human Oct3/4, also known as *Homo sapiens* POU class 5 homeobox 1 (POU5F1) the sequence of which may be found at GenBank Accession Nos. NP_002692 (SEQ ID NO: 9) and NM_002701 (SEQ ID NO: 10). Oct3/4 polypeptides, e.g. those that are at least 70%, 75%, 80%, 85%, 90%, 91%, 92%, 95%, 97%, 99%, or 100% identical to the sequence provided in GenBank Accession No. NM_002701 (SEQ ID NO: 10), and the nucleic acids that encode them find use as a reprogramming factor in the present invention.

A Sox2 polypeptide is a polypeptide comprising the amino acid sequence at least 70% identical to the amino acid sequence of human Sox2, i.e., sex-determining region Y-box 2 protein, the sequence of which may be found at GenBank Accession Nos. NP_003097 (SEQ ID NO: 11) and NM_003106 (SEQ ID NO: 12). Sox2 polypeptides, e.g. those that are at least 70%, 75%, 80%, 85%, 90%, 91%, 92%, 95%, 97%, 99%, or 100% identical to the sequence provided in GenBank Accession No. NM_003106 (SEQ ID NO: 12), and the nucleic acids that encode them find use as a reprogramming factor in the present invention.

The methods of the current disclosure may also include contacting the mammalian somatic cell with a small molecule or reprogramming enhancer that can alter or modulate transcription. In some examples, the small molecule or reprogramming enhancer is a histone deacetylase (HDAC) inhibitor. Small molecules, including without limitation siRNAs, valproic acid, hydroxamic acid, trichostatin A, suberoylanilide hydroxamic acid, BIX-01294 and BayK8644 have been described as useful in reprogramming cells (see, e.g., Shi et al., Cell Stem Cell 2008; 3(5):568-574 and Huangfu et al., Nature Biotechnology 2008, 26:795-797, each herein specifically incorporated by reference). Other reprogramming enhancers useful in the methods of the current disclosure include aluminum-containing salts (e.g., aluminum hydroxide) and TGF-beta inhibitors (e.g., A83-01).

Synthetic Transcription Factor

Generally, the term "transcription factor" refers to a complex which has the ability to bind to DNA (via a DNA-binding domain) and to effect regulation of gene expression via a functional (activation or repressor) domain. In connection with the current disclosure, the DNA-binding domain may be replaced with an RNA-binding domain (e.g., dCAS9), which is used in combination with a (DNA-binding) guide RNA (gRNA). An exemplary synthetic transcription factor of the current disclosure includes a gRNA and dCas9-VP64, wherein dCas9 is an exemplary RNA-binding domain and VP64 is an exemplary transactivation domain. Another exemplary synthetic transcription factor of the current disclosure includes a gRNA (including at least one MS2 binding loop); dCas9; and MS2-VP64, wherein MS2 is an exemplary RNA-binding domain, and VP64 is an exemplary transactivation domain.

Thus, a synthetic transcription factor of the current disclosure includes (a) at least one guide RNA (gRNA) comprising a DNA-binding segment and a polypeptide-binding segment, and (b) at least one transcriptional modulator, a polypeptide, which includes an RNA-binding domain (capable of binding the polypeptide-binding segment of the gRNA) and at least one functional domain (e.g., a transcriptional activation domain). Based on the interaction between the gRNA and the transcriptional modulator, the transcriptional modulator is targeted to a specific DNA location within the cellular genome (e.g., the promoter region of an endogenous pluripotency factor gene). Subsequently, the recruitment of the transcriptional modulator modulates expression of the endogenous gene, e.g., driving the expression of a pluripotency factor gene, thereby contributing to the reprogramming of the cell.

To modulate gene expression at multiple loci within the genome of the cell, the cells may be contacted with a cocktail of synthetic transcription factors. For example, the cocktail may include a multitude of guide RNAs, each having a different DNA-binding segment, but each having the same polypeptide-binding segment. In this case, the same transcriptional modulator can be used to modulate multiple genes. In other examples, the cocktail of synthetic transcription factors can includes at least two guide RNAs having different polypeptide-binding segments, in which case at least two different transcriptional modulators having different RNA-binding domains are used.

Guide RNA

The RNA molecule that binds to the transcriptional modulator and targets the transcriptional modulator to a specific location within the target DNA (i.e., the promoter region of an endogenous pluripotency factor gene), is referred to herein as "guide RNA" or "gRNA," and may also be referred to herein as a "DNA-targeting RNA." A guide RNA comprises at least two nucleotide segments: at least one "DNA-binding segment" and at least one "polypeptide-binding segment." By "segment" is meant a part, section, or region of a molecule, e.g., a contiguous stretch of nucleotides of an RNA molecule. The definition of "segment," unless otherwise specifically defined, is not limited to a specific number of total base pairs.

The guide RNA can include at least two polypeptide-binding segments. In some embodiments, a first polypeptide-binding segment of the guide RNA is designed to bind a first transcriptional modulator (e.g., dCas9-VP64) or dCas9 alone, and a second polypeptide-binding segment designed to recruit a second transcriptional modulator. For example, a first polypeptide-binding segment of the guide RNA binds a synthetic dCas9-based transcriptional regulator (e.g., dCas9-VP64), while one or more MS2-recruiting polypeptide-binding segments (e.g., fused to the tetra-loop and/or stem loop2 domains) of the guide RNA bind one or more MS2-based transcriptional modulators (e.g., MS2-VP64). See, e.g., Konermann et al., *Nature* 2015, 517: 583-588 (and supporting material), the disclosure of which is incorporated herein in its entirety. In some examples, the somatic cell is contacted with dCas9, a MS2-based transcriptional regulator, and a guide RNA, which binds both dCas9 and MS2.

A polypeptide-binding segment of the gRNA may comprise regions of more than one nucleic acid molecule. In some cases the polypeptide-binding segment of a guide RNA comprises two separate molecules hybridized along a region of complementarity. For example, a polypeptide-binding segment of a guide RNA that comprises two separate molecules can comprise (i) 30 base pairs of a first RNA molecule that is 100 base pairs in length, and 15 base pairs of a second RNA molecule that is 50 base pairs in length.

The guide RNA can be introduced into the target cell as an isolated RNA molecule, or is introduced into the cell using an expression vector containing DNA encoding the guide RNA.

DNA-Binding Segment of the Guide RNA

The "DNA-binding segment" (or "DNA-targeting sequence") of the guide RNA comprises a nucleotide sequence that is complementary to a specific sequence within a target DNA. In some embodiments of the present disclosure, the target DNA is the promoter region of an endogenous reprogramming factor gene or other pluripotency factor gene. For example, the DNA-binding segment of the guide RNA is complementary to a sequence within the promoter region of the endogenous oct3/4 gene, the endogenous sox-2 gene, the endogenous klf4 gene, or the endogenous c-myc gene. In other examples, the DNA-binding segment is derived from a library of nucleotide sequences and may bind the promoter region of a candidate pluripotency factor gene.

Polypeptide-Binding Segment of the Guide RNA

The guide RNA of the current disclosure includes one or more polypeptide-binding sequences/segments. The polypeptide-binding segment (or "protein-binding sequence") of the guide RNA interacts with the RNA-binding domain of a transcriptional modulator of the current disclosure (e.g., a modified Cas9 polypeptide domain or a MS2 polypeptide domain). Such polypeptide-binding segments or sequences are known to those of skill in the art, e.g., those disclosed in U.S. patent application publications 2014/0068797, 2014/0273037, 2014/0273226, 2014/0295556, 2014/0295557, 2014/0349405, 2015/0045546, 2015/0071898, 2015/0071899, and 2015/0071906, the disclosures of which are incorporated herein in their entireties.

In some examples, the guide RNA includes at least one dCas9-binding segment. Using the traditional CRISPR system, dCas9 is required to form a DNA-binding complex with the guide RNA before the resulting complex can efficiently bind DNA. Thus, in some examples, the synthetic transcription factor includes at least one dCas9-based transcriptional modulator (e.g., dCas9 fused to a transactivation or repressor domain). However, guide RNAs, which do not rely on Cas9 binding may be designed.

In other examples, the guide RNA includes at least two polypeptide binding segments: a first polypeptide binding segment that is a dCas9-binding segment, and a second polypeptide binding segment that binds a polypeptide other than dCas9 (e.g., MS2). In this case, dCas9 may be provided to the cell on its own (without being fused to a transcriptional activation or repressor domain).

In some examples, the polypeptide-binding segment of the guide RNA is a MS2-binding segment, which may, e.g., be fused to the tetra-loop and/or stem loop2 domains of the guide RNA. Such binding domains are known to those of skill in the art. See, e.g., Konermann et al., *Nature* 2015, 517: 583-588 (and supporting material), the disclosure of which is incorporated herein in its entirety.

Transcriptional Modulator

A transcriptional modulator of the current disclosure includes at least one RNA-binding domain (capable of binding the polypeptide-binding segment of the guide RNA), and at least one functional domain (e.g., a transcriptional activation domain or a repressor domain). Based on the interaction between the RNA-binding domain of the transcriptional modulator and the guide RNA, the transcriptional modulator is targeted to a specific gene of interest, a DNA location within the cellular genome (e.g., the promoter region of an endogenous reprogramming factor gene). Recruitment of the transcriptional modulator to the endogenous gene of interest modulates expression of the target gene, thereby contributing to cellular reprogramming. Such modulation can substitute for the expression of an exogenous reprogramming factor gene. For example, instead of introducing exogenous Oct3/4 into the cell, e.g., via an expression vector encoding the polypeptide, the endogenous oct3/4 gene is activated directly in the cell.

RNA-Binding Domain (BD) of the Transcriptional Modulator

RNA-binding domains or RNA-binding polypeptides are known to those of skill in the art, e.g., those disclosed in U.S. patent application publications 2014/0068797, 2014/0273037, 2014/0273226, 2014/0295556, 2014/0295557, 2014/0349405, 2015/0045546, 2015/0071898, 2015/0071899, and 2015/0071906, the disclosures of which are incorporated herein in their entireties. In some embodiments of the current disclosure the RNA-binding domain includes an enzymatically inactive Cas9 polypeptide (dCas9). In some examples, in which the RNA binding domain of the transcriptionsl modulator is not dCas9 (e.g., MS2), the cell is additionally provided dCas9, e.g., because dCas9 is required to form a DNA-binding complex with the guide RNA. Alternatively, the cell is contacted with at least two transcriptional modulators, at least one of which is dCas9-based. In some examples, the RNA-binding domain of the transcriptional modulator includes a MS2 polypeptide.

The RNA-binding domain of the transcriptional modulator is typically fused to at least one functional domain, e.g., a transactivation domain, such as VP64, p65, or HSF1. In some examples, an RNA-binding domain, such as dCas9 or MS2 is fused to exactly one functional domain. For example, a transcriptional modulator of the current disclosure may have the general structure: dCas9-VP64 or MS2-p65 in combination with dCas9. In other examples, a single RNA-binding domain, such as dCas9 or MS2 is fused to multiple functional domains, wherein each functional domain is independently selected. If the transcriptional modulator includes at least two functional domains, the functional domains may be attached to the RNA-binding domain in a linear fashion. For example, a transcriptional modulator of the current disclosure may have the general structure: MS2-p65-HSF1.

Functional Domain (FD) of the Transcriptional Modulator

The transcriptional modulators of the current disclosure include at least one functional domain. A functional domain can be any domain which can control the rate of transcription of genetic information from DNA to messenger RNA. The functional domain may perform this function alone or with other proteins in a complex, by promoting (as an activator), or blocking (as a repressor) the recruitment of RNA polymerase (the enzyme that performs the transcription of genetic information from DNA to RNA). Such transcription activation domains, which are normally part of DNA-binding transcription factors, are known to those of ordinary skill in the art. In some embodiments of the current disclosure the functional domain is selected from VP64, p65, and the activation domain of HSF-1 (human heat shock factor 1) (activator of gene expression) or KRAB (suppressor of gene expression).

In some embodiments, the functional domain (e.g., the transcription activation domain or repressor domain) is fused to the amino- or carboxy-terminus of the RNA-binding domain. In some examples, the RNA-binding domain is dCas9, and the functional domain (e.g., a transcription activation domain) is fused to the C- or N-terminus of the dCas9 polypeptide. In other examples, the functional domain (e.g., the transcription activation domain) is fused to an internal amino acid residue of the RNA-binding domain. In other examples, the RNA-binding domain is fused to an internal amino acid residue of the functional domain.

In some examples, the methods of the present disclosure utilize at least two transcriptional modulators to modulate the expression of a single gene. An example of such combination involves dCas9-VP64 and MS2-p65-HSF1in combination with a gRNA, which can bind both, dCas9 and MS2. See, e.g., Konermann et al. supra.

Exemplary transcriptional modulator combinations include:

1. dCas9-[(FD$^1$)$_m$-FD]$_n$;
2. BD$^1$-[(FD$^1$)$_m$-(FD)]$_n$ in combination with dCas9; and
3. BD$^1$-[(FD$^1$)$_m$-(FD)]$_n$ in combination with dCas9-[(FD')$_m$-(FD)]$_n$, wherein BD$^1$ is an RNA-binding domain other than dCas9; FD$^1$ and FD are independently selected functional domains, which may be the same or different; m is an integer independently selected from 0 and 1; and n is an integer independently selected from 1 to 10. In one example in the above embodiments, the integer n is independently selected from 1 to 5 (e.g., 1 or 2). In another example, n at each occurrence is 1. In another example in the above embodiments, m is 0.

Reprogramming

Methods for introducing the synthetic transcription factors (including guide RNA and transcriptional modulators) to somatic cells include providing a cell with purified RNA or polypeptides; or with nucleic acids encoding the polypeptides.

Many vectors useful for transferring exogenous genes into target mammalian cells are available. The vectors may be maintained episomally, e.g. as plasmids, or virus-derived vectors such as cytomegalovirus, adenovirus, etc. Expression vectors for the synthetic transcription factors typically comprise suitable promoters for driving the expression of the desired genes, i.e., transcriptional activation. This may include ubiquitously acting promoters, for example, the CMV-beta-actin promoter, or inducible promoters, such as promoters that are active in particular cell populations or that respond to the presence of drugs such as tetracycline. By transcriptional activation, it is intended that transcription will be increased above basal levels in the target cell by at least or about 2, 3, 4, 5, 6, 7, 8, 9, 10, 100 or 1000 fold.

For example, to prepare human iPSCs, the starting somatic cells (e.g., human PBMNCs) are cultured, and transfected by nucleofection with a predetermined vector combination to induce reprogramming. In some examples, the vector(s) are episomal plasmids.

For example, cryopreserved starting cells may be collected by centrifugation and be seeded onto tissue culture plates (e.g., 6-well plates; at 2-4×10$^6$ cells/ml), and grown under appropriate conditions, e.g., in a humidified 37° C. incubator under normoxic conditions (e.g., 20.9% 02; 5% $CO_2$).

After a certain growth period (e.g., about 3 days) the cells may be collected by centrifugation, suspended in an appropriate growth medium (e.g., PBMC medium, containing all supplements), and counted. Cells may subsequently be seeded onto tissue culture plates (e.g., 6-well plates at 0.5-1×10$^6$ cells/ml), and grown under appropriate conditions, e.g., in a humidified 37° C. incubator under normoxic conditions (20.9% 02; 5% $CO_2$).

After an appropriate growth period (e.g., about 6 days) cells may be subjected to nucleofection in an appropriate medium (e.g., 100 μl Lonza P3 Nucleofector™ Solution) containing the reprogramming plasmids under appropriate conditions (e.g., using LONZA 4D Nucleofector™).

Following nucleofection, the somatic cells may be maintained in a conventional culture medium comprising feeder layer cells, or may be cultured in the absence of feeder layers, i.e. lacking somatic cells other than those being induced to pluripotency. Feeder layer free cultures may utilize a protein coated surface, e.g. matrigel, etc. The somatic cells may also be maintained in suspension or attached to microcarriers.

For example, after nucleofection, the cells may be diluted using an appropriate medium (e.g., PBMC medium containing all supplement), and transferred to an appropriate tissue culture plate in an appropriate medium supporting reprogramming (e.g., 6-well plate, Lonza L7 hPSC Matrix™, PBMC medium, containing all supplements, optionally containing a reprogramming enhancer, such as Lonza episomal Enhancer ATM). Cells may subsequently be grown under appropriate conditions, e.g., in a hypoxic humidified incubator at 37° C. (3% 02; 5% $CO_2$) for an appropriate amount of time (e.g., about two days), thereby allowing reprogramming of the cells.

After an appropriate growth period (e.g., about two days after nucleofection), an appropriate culture medium supporting iPSC growth and colony formation (e.g., Lonza L7 hPSC Culture Medium™, containing supplement) is added to the nucleofected cells. Thereafter (e.g., about four days after nucleofection) the medium is replaced with an appropriate culture medium supporting iPSC growth and colony formation (e.g., Lonza L7 hPSC Culture Medium™ containing supplement). The cells may subsequently be grown under appropriate conditions, e.g., in a hypoxic humidified incubator at 37° C. (3% 02; 5% $CO_2$) for an appropriate amount of time (e.g., about 14 days).

The medium may be replaced as needed until iPSC colonies are large enough to subculture. Initial iPSC colonies may be passaged manually into separate wells (e.g., L7 hPSC Matrix™) using an appropriate medium (e.g., L7 hPSC Culture Medium™, containing supplement) and incubated under appropriate conditions, e.g., in a humidified 37° C. incubator under normoxic conditions (20.9% 02; 5% $CO_2$). For subsequent passages of iPSCs (e.g., P3 and later passages) an appropriate passaging solution may be used (e.g., Lonza L13 hPSC Passaging Solution™).

In some embodiments, the population of somatic cells is further contacted with an exogenous reprogramming factor. A starting population of somatic cells is contacted with reprogramming factors, as defined above, in a combination and quantity sufficient to reprogram the cell to pluripotency. Reprogramming factors may be provided to the somatic cells individually or as a single composition, that is, as a premixed composition, of reprogramming factors. The reprogramming factors may be added to the subject cells simultaneously or sequentially at different times. The dose of reprogramming factors will vary with the nature of the cells, the factors, the culture conditions, etc. In some embodiments the dose will be from about 1 nM to about 1 μM for each factor, more usually from about 10 nM to about 500 nM, or around about 100 to 200 nM.

In some embodiments, a reprogramming factor polypeptide will comprise the polypeptide sequences of the reprogramming factor fused to a polypeptide permeant domain. A number of permeant domains, such as polypeptides, peptidomimetics, and non-peptide carriers, are known in the art and may be used in the in the present invention. For example, a permeant polypeptide may be derived from the third alpha helix of *Drosophila melanogaster* transcription factor Antennapaedia, referred to as penetratin.

Reprogramming efficiency may be determined by colony count (e.g., by morphology or alkaline phosphatase staining).

iPSCs may have an hESC-like morphology, growing as flat colonies with large nucleo-cytoplasmic ratios, defined borders and prominent nuclei. In addition, the iPSCs may express one or more key pluripotency markers known by one of ordinary skill in the art, including but not limited to alkaline phosphatase, SSEA3, SSEA4, Sox2, Oct3/4, Nanog, TRA160, TRA181, TDGF 1, Dnmt3b, FoxD3, GDF3, Cyp26a1, TERT, and zfp42. In addition, the iPSCs are capable of forming teratomas. In addition, they are capable of forming or contributing to ectoderm, mesoderm, or endoderm tissues in a living organism.

Genes may be introduced into the somatic cells or the iPSCs derived therefrom for a variety of purposes, e.g. to replace genes having a loss of function mutation, provide marker genes, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to introduce nucleic acids into the target cells, e.g. electroporation, calcium precipitated DNA, fusion, transfection, lipofection, infection and the like, as discussed above. The particular manner in which the DNA is introduced is not critical to the practice of the invention.

In some aspects, the present disclosure provides iPS cells made according to a method disclosed herein.

Methods of Use

The iPSCs produced by the above methods may be used for reconstituting or supplementing differentiating or differentiated cells in a recipient. The induced cells may be differentiated into cell-types of various lineages. Examples of differentiated cells include any differentiated cells from ectodermal (e.g., neurons and fibroblasts), mesodermal (e.g., cardiomyocytes), or endodermal (e.g., pancreatic cells) lineages. The differentiated cells may be one or more: pancreatic beta cells, neural stem cells, neurons (e.g., dopaminergic neurons), oligodendrocytes, oligodendrocyte progenitor cells, hepatocytes, hepatic stem cells, astrocytes, myocytes, hematopoietic cells, or cardiomyocytes.

There are numerous methods of differentiating the induced cells into a more specialized cell type. Methods of differentiating induced cells may be similar to those used to differentiate stem cells, particularly ES cells, MSCs, MAPCs, MIAMI, hematopoietic stem cells (HSCs). In some cases, the differentiation occurs ex vivo; in some cases the differentiation occurs in vivo.

The induced cells, or cells differentiated from the induced cells, may be used as a therapy to treat disease (e.g., a genetic defect). In some aspects the current disclosure provides methods of treating a disease amenable to stem cell therapy in a patient. Exemplary methods include administering to a patient in need thereof a therapeutically effective amount of a pharmaceutical composition comprising an iPS cell of the present disclosure and a pharmaceutically acceptable carrier.

The therapy may be directed at treating the cause of the disease; or alternatively, the therapy may be to treat the effects of the disease or condition. The induced cells may be transferred to, or close to, an injured site in a subject; or the cells can be introduced to the subject in a manner allowing the cells to migrate, or home, to the injured site. The transferred cells may advantageously replace the damaged or injured cells and allow improvement in the overall condition of the subject. In some instances, the transferred cells may stimulate tissue regeneration or repair.

The transferred cells may be cells differentiated from induced cells. The transferred cells also may be multipotent stem cells differentiated from the induced cells. In some cases, the transferred cells may be induced cells that have not been differentiated.

The number of administrations of treatment to a subject may vary. Introducing the induced and/or differentiated cells into the subject may be a one-time event; but in certain situations, such treatment may elicit improvement for a limited period of time and require an on-going series of repeated treatments. In other situations, multiple administrations of the cells may be required before an effect is observed. The exact protocols depend upon the disease or condition, the stage of the disease and parameters of the individual subject being treated.

The cells may be introduced to the subject via any of the following routes: parenteral, intravenous, intraarterial, intramuscular, subcutaneous, transdermal, intratracheal, intraperitoneal, or into spinal fluid.

The iPSCs may be administered in any physiologically acceptable medium. They may be provided alone or with a suitable substrate or matrix, e.g. to support their growth and/or organization in the tissue to which they are being transplanted. Usually, at least $1 \times 10^5$ cells will be administered, preferably $1 \times 10^6$ or more. The cells may be introduced by injection, catheter, or the like. The cells may be frozen at liquid nitrogen temperatures and stored for long periods of time, being capable of use on thawing. If frozen, the cells will usually be stored in a 10% DMSO, 50% FCS, 40% RPMI 1640 medium. Once thawed, the cells may be expanded by use of growth factors and/or stromal cells associated with progenitor cell proliferation and differentiation.

Example 1

Reprogramming Rescue by Endogenous Activation of the Human POU5F1/OCT4 Gene Transcription (CRISPR-Based Reprogramming)
Vector Sequences DNA sequences for dCas9, dCas9-VP64 and guide RNA constructs were prepared as described in Mali, P. et al. "CAS9 transcriptional activators for target specificity screening and paired nickases for cooperative genome engineering." Nat Biotechnol 2013, 31(9): 833-8, the disclosure of which is incorporated herein in its entirety. Additional sequences for gRNAs containing MS2 binding loops and the MS2-transcriptional regulator fusion proteins (e.g. MS2-VP64) were prepared as described in Konermann et al., Nature 2015, 517: 583-588 (and supporting material), the disclosure of which is incorporated herein in its entirety. Sequences were synthesized by GeneART and cloned into episomal cloning vectors. These vectors were used directly in the following experiments.

Selection of gRNA for Human POU5F1/OCT4 Transcription Activation

Human peripheral blood mononuclear cells (hPBMCs) were cultured for 6 days, then transfected with various combinations of dCas9 and gRNA encoding vectors (see Table 1 below). Transfections were accomplished by nucleofecting $10^6$ cells which each plasmid combination using Lonza 4D Nucleofector™ (program EO-115) and Lonza P3 Primary Cell 4D-Nucleofector™ Kit. Cells were plated in completed HPGM and cultured for an additional 48 hours. Cell pellets were harvested, total RNA was purified and qt-PCR was performed to detect endogenous levels of human POU5F1/OCT4 mRNA.

TABLE 1

Vector Combinations

| Condition# | Description | µg Cas9:gRNA |
|---|---|---|
| 1-2 | dCas9 No gRNA | 0.8:0 |
| 3-4 | dCas9-VP64 No gRNA | 0.8:0 |
| 5-6 | dCas9 18 + 20 gRNA | 0.8:0.8 (0.4 of each gRNA) |
| 7-8 | dCas9-VP64 18 + 20 gRNA | 0.8:0.8 (0.4 of each gRNA) |
| 9-10 | dCas9 15-21 gRNA | 0.8:0.8 (0.11 of each gRNA) |
| 11-12 | dCas9-VP64 15-21 gRNA | 0.8:0.8 (0.11 of each gRNA) |
| 13-14 | dCas9 MS2-VP64 | 0.8:0.8 |
| 15-16 | dCas9 Oct4 gRNA (MS2 loop v2.0) MS2-VP64 | 0.8:0.4:0.4 |
| 17-18 | dCas9 Oct4 gRNA (MS2 loop v2.0) VP64-MS2-VP64 | 0.8:0.4:0.4 |
| 19-20 | dCas9 Oct4 gRNA (MS2 loop v2.0) p65-MS2-HSF1 | 0.8:0.4:0.4 |

Feeder-Independent Reprogramming of Human PBMCs hPBMNCs were nucleofected to induce reprogramming using the below described protocol and the following vector combinations: (a) five vectors encoding for: 1. Oct4; 2. Sox-2 and Klf4; 3. Lin28 and c-Myc; 4. P53DD; 5. EBNA-1 positive control ("Okita set"); (b) Okita set without the vector that encodes for Oct4; and (c) Okita set without the vector that encodes for Oct4, along with the above vector encoding Cas-9-VP64 and gRNA found to induce Oct4 transcription.

Reprogramming efficiency was determined by colony count (either by morphology or alkaline phosphatase staining) and colony quality (by morphology).

Using the below procedure and the above described episomal plasmids, human induced pluripotent stem cells (iPSCs) were generated by reprogramming human PBMCs.

Materials: hPBMCs (Lonza Cat. CC-2702, ($50 \times 10^6$ cells/vial); Lonza L7 hPSC Culture Medium™ and Supplement Kit; Lonza L13 hPSC Passaging Solution™; Lonza L7 hPSC Matrix™; Lonza 4D Nucleofector™; Lonza P3 Primary Cell 4D-Nucleofector™ Kit; Lonza Episomal Reprogramming Kit™ (Episomal Reprogramming Plasmid Mix™; Episomal Enhancer ATM); 6- and 12-well tissue culture treated plates; PBMC Basal Medium; HPGM™; Poietics™ hematopoietic progenitor growth medium without antibiotics; PBMC Medium Supplements (see Table 2).

TABLE 2

| | PBMC Medium Supplements | | |
|---|---|---|---|
| Component | Vendor | Stock Conc. | Final Conc. |
| 1-Thioglycerol | Sigma #M6145 | | 200 µM |
| Holo-transferrin | R&D Systems #2914-HT | 20 mg/ml | 100 µg/ml |
| Dexamethasone | Sigma #D1756 | 10 mM (10,000×) | 1 µM |
| SCF | PeproTech #300-07 | 100 ug/ml (2,000×) | 100 ng/ml |
| EPO | R&D Systems #287-TC-500 | 2 U/µl (1,000×) | 2 U/ml |
| IL-3 | PeproTech #200-03 | 10 µg/ml | 10 ng/ml |
| IGF-1 | Peprotech #100-11 | 40 ng/µl | 40 ng/ml | hPBMCs were centrifuged in basal PBMC medium (200×g for 15 minutes). The medium was removed, and the cell pellet dispersed in 10 ml PBMC medium, containing all supplements. The cells were counted and seeded onto a 6-well, tissue culture treated plate at 2-4×10$^6$ cells/ml. The plate was placed into a humidified 37° C. incubator and kept under normoxic conditions (20.9% 02; 5% CO$_2$).

On day 3, the cells were transferred to a 15 ml centrifuge tube using basal PBMC medium and centrifuged at 200×g for 5 minutes. The media was removed and the cell pellet suspended in 10 ml PBMC medium, containing all supplements. The cells were counted and seeded onto a 6-well plate at 0.5-1×10$^6$ cells/ml. The plate was placed into a humidified 37° C. incubator under normoxic conditions (20.9% 02; 5% CO$_2$)

On day 6, 2 ml PBMC Medium, containing all supplements, was added to each well of a 6-well plate (pre-treated with L7 hPSC Matrix™). 6 µl Episomal Enhancer ATM was added to each well. The plates were pre-equilibrated in a hypoxic humidified incubator at 37° C. (3% 02; 5% CO$_2$) for one hour. 1×10$^6$ cells in basal PBMC were transferred to a 15 mL tube and centrifuged at 200×g for 5 minutes. The supernatant was removed, and the cells were suspended in nucleofection reagent (100 µl P3 Nucleofector™ Solution pipetted into a tube containing 3 ug of Episomal Reprogramming Plasmid Mix™).

The cells were transferred to a Nucleocuvette™ and nucleofected (4D Nucleofector™) Approximately 500 µl of PBMC medium (containing all supplements) was added to the cuvette, and the cells were transferred directly onto the equilibrated 6-well plate. The plate was placed into a hypoxic humidified incubator at 37° C. (3% 02; 5% CO$_2$) for two days.

On day 8, 2 ml of L7 hPSC Culture Medium™ (containing supplement) were added to each well with nucleofected cells. The cells were cultured in L7 hPSC Culture Medium™ under hypoxic conditions, until colonies were large enough to subculture.

Subculturing iPSC Colonies

A 12-well plate was pre-treated with L7 hPSC Matrix™, and the initial colonies were seeded into separate wells using L7 hPSC Culture Medium™, containing supplement. The plate was incubated in a humidified 37° C. incubator under normoxic conditions (20.9% 02; 5% CO$_2$). For P3 and later passages, L13 hPSC Passaging Solution™ was used.

Example 2

Reprogramming Rescue by Endogenous Activation of the Human OCT4 Gene Transcription (CRISPR-Based Reprogramming)

Vector Sequences

DNA sequences for dCas9-VPR consisting of VP64-p65-Rta activation domains fused to the C-terminus of dCas9 protein and guide RNA constructs were prepared as described in Mali, P. et al. (Mali, P. et al. "CAS9 transcriptional activators for target specificity screening and paired nickases for cooperative genome engineering." Nat Biotechnol 2013, 31(9): 833-8) and Chavez, A. et al. (Chavez, A. et al. "Highly efficient Cas9-mediated transcriptional programming." Nat Methods. 2015 April; 12(4):326-8). Sequences were synthesized by GeneART and cloned into standard cloning vectors. These vectors were used directly in the following experiments.

Determining gRNA Combination for Human OCT4 Transcription Activation

HEK293T cells were transfected with various combinations of transient Cas9-VPR and gRNA encoding vectors (see Table 1). The plasmids were co-transfected into HEK293T cells using Lipofectamine 2000® reagent. Cell pellets were harvested 48 hours post transfection. Total RNA was purified and qRT-PCR was performed to detect endogenous levels of hOCT4 mRNA.

TABLE 1

Transfections for determining the optimal gRNA combination for hOCT4 transcription activation in HEK293T cells

| Condition# | Description | Plasmid ratio (µg) |
|---|---|---|
| 1-3 | dCas9-VPR w/o gRNA | 1:0 |
| 4-6 | dCas9-VPR 18 + 20 gRNA | 1:1 (0.5 of each gRNA) |
| 7-9 | dCas9-VP64 15-21 gRNA | 1:1 (0.11 of each gRNA) |

High levels of hOCT4 mRNA were produced by dCas9-VPR co-transfected with two gRNAs (18+20) or seven gRNAs (15-21) (~360-fold and ~1380-fold, respectively, see FIG. 1). The endogenous levels of human POU5F1/OCT4 mRNA in control iPSC cells were ~5900-fold higher than the baseline. Although the higher levels of hOCT4 mRNA were detected using seven gRNAs (15-21), the large size of the plasmid could influence the efficiency of transfection in future reprogramming experiments. Therefore the decision was made to use the combination of two gRNAs (18+20) for generating episomal CRISPR vector for reprogramming experiments.

Figure 2:
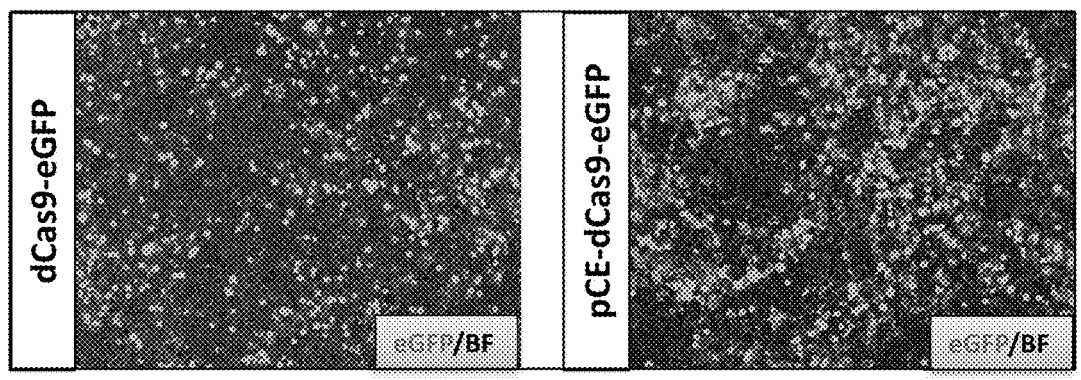
FIG. 2. Upregulation of endogenous hOCT4 by transient and episomal CRISPR vectors in HEK293T cells. A. Transfection efficiency with transient dCas9-eGFP and episomal pCE-dCas9-eGFP vectors shown by immunofluorescence analysis. B. Relative mRNA expression levels were measured by qRT-PCR 48 hours post transfection. The OCT4 mRNA level in untransfected HEK293T cells was used as baseline. Data represent mean±stdv, n=2 independent transfections.
Figure 2:
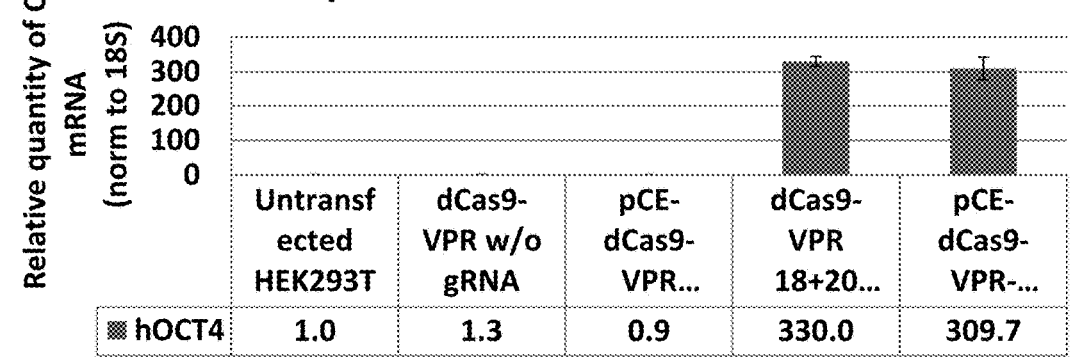

Generating Episomal CRISPR Vector for Activation of Endogenous Human POU5F1/OCT4 Gene Transcription Episomal CRISPR vector for hOCT4 transcription activation was generated by cloning of dCas9-VPR and gRNAs 18+20 synthesized by GeneArt into pCE episomal vector (pCE-dCas9-VPR-OCT4). In addition, the vector expressing dCas9-eGFP fusion protein was generated to serve as a transfection control (pCE-dCas9-eGFP). The function of the episomal vector pCE-dCas9-VPR-OCT4 was validated in HEK293T cells using immunofluorescence analysis and qRT-PCR. Similar transfection efficiency was achieved in HEK293T cells with transient dCas9-eGFP and episomal pCE-dCas9-eGFP vectors (FIG. 2A). Similar activation of hOCT4 in HEK293T cells was achieved with episomal and transient CRISPR-hOCT4 vectors (FIG. 2B). Episomal dCas9-eGFP and pCE-dCas9-eGFP vectors were used directly in the following experiments.

Reprogramming Rescue by CRISPR-Mediated Activation of Endogenous Human OCT4 Gene Transcription To demonstrate that CRISPR technology can be used to replace exogenous OCT4 in human cell reprogramming, two types of human somatic cells, human foreskin fibroblast cells (HFFs) and peripheral blood mononuclear cells (PBMNCs), were reprogrammed using episomal vector encoding for dCas9-VPR and gRNAs for hOCT4 activation (pCE-dCas9-VPR-OCT4) along with episomal OKITA vectors (vectors comprising oriP/EBNA-1; Okita et al., *Stem Cells* 31: 458-466 (2013); Okita et al., *Nature Methods* 8:409-412 (2011)) encoding for SOX2, KLF4, LIN28 and L-MYC (OKITA set w/o pCE-hOCT3/4). As a positive control for CRISPR-mediated reprogramming, somatic cells were transfected with episomal OKITA vectors encoding for OCT4, SOX2, KLF4, LIN28 and L-MYC (full OKITA set). Transfections were accomplished by nucleofecting somatic cells with each plasmid combination (see Table 2) using Lonza 4D Nucleofector™ (program EO-115) and Lonza P3 Primary Cell 4D-Nucleofector™ Kit.

TABLE 2

Reprogramming rescue by CRISPR-mediated activation of endogenous hOCT4 gene transcription

| Condition# | Description | Plasmid ratio (µg) | |
|---|---|---|---|
| 1-2 | Okita set w/o pCE-hOCT4 + pCE-dCas9-eGFP | Okita 1.05 of each, 0.85 of EBNA:2 | |
| 3-4 | Okita set w/o pCE-hOCT4 + pCE-dCas9-VPR-OCT4 | Okita 1.05 of each, 0.85 of EBNA:2 | |
| 5-6 | Full Okita set | Okita 1.05 of each, 0.85 of EBNA | |

Figure 3:
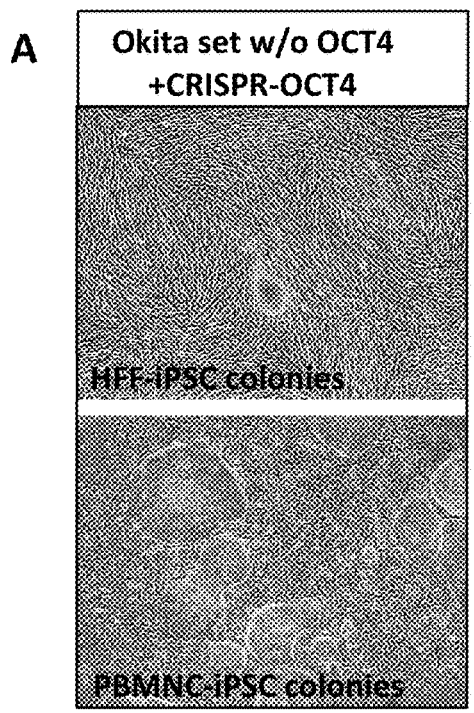
FIG. 3. Endogenous activation of OCT4 by CRISPR can 'rescue' reprogramming in the absence of exogenous OCT4. iPSC colonies generated from reprogramming HFF and PBMNCs using CRISPR technology are shown (A). The phase-contrast images of HFF-iPSC and PBMNC-iPSC colonies were taken 20 and 16 days post nucleofection, respectively, before colony picking. Reprogramming efficiency was determined by counting the number of iPSC colonies either by morphology for HFF-iPSCs or alkaline phosphatase staining for PBMNC-iPSCs (B).
Figure 3:
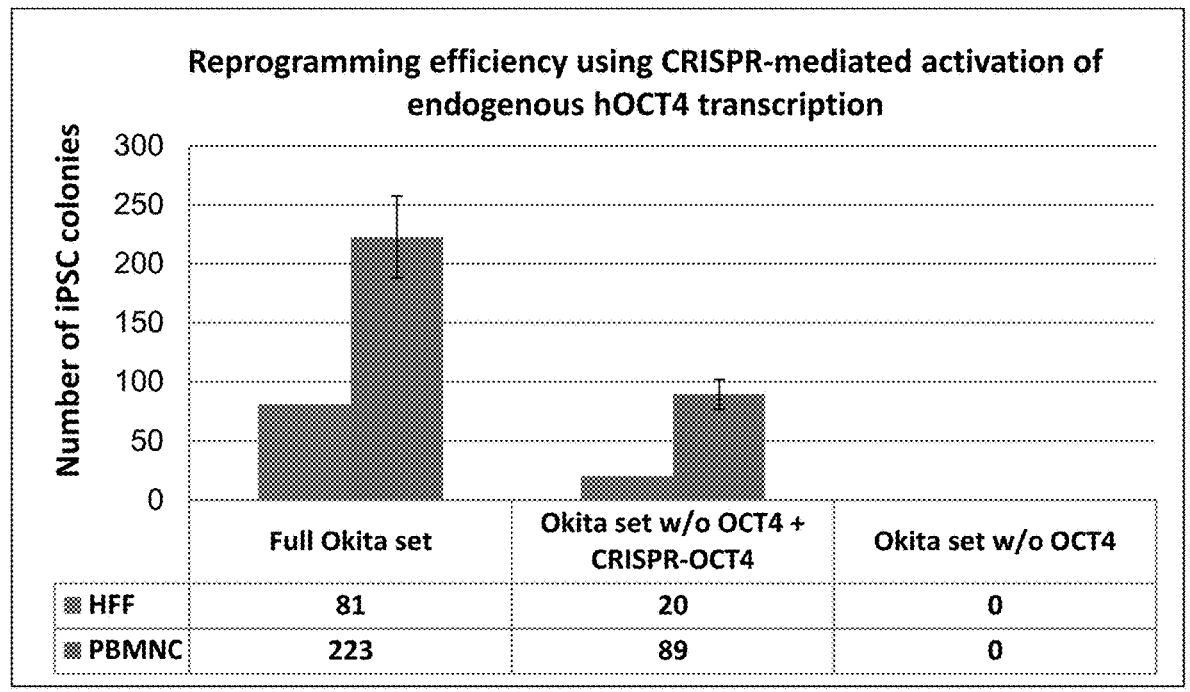

Using the transfection procedure described above, human induced pluripotent stem cells (iPSCs) were generated by reprogramming both HFFs and PBMNCs. Reprogramming efficiency was determined by colony count (see FIG. 3A). In general, higher reprogramming efficiency was achieved in PBMNCs compared to HFFs. Reprogramming using pCE-dCas9-VPR-OCT4 (CRISPR-OCT4) vector was lower in both HFFs and PBMNCs (~4-fold and ~2.5-fold, respectively, see FIG. 3B) compared to reprogramming using full Okita set. These results indicate that endogenous activation of OCT4 by CRISPR can 'rescue' reprogramming in the absence of exogenous OCT4.

Figure 4:
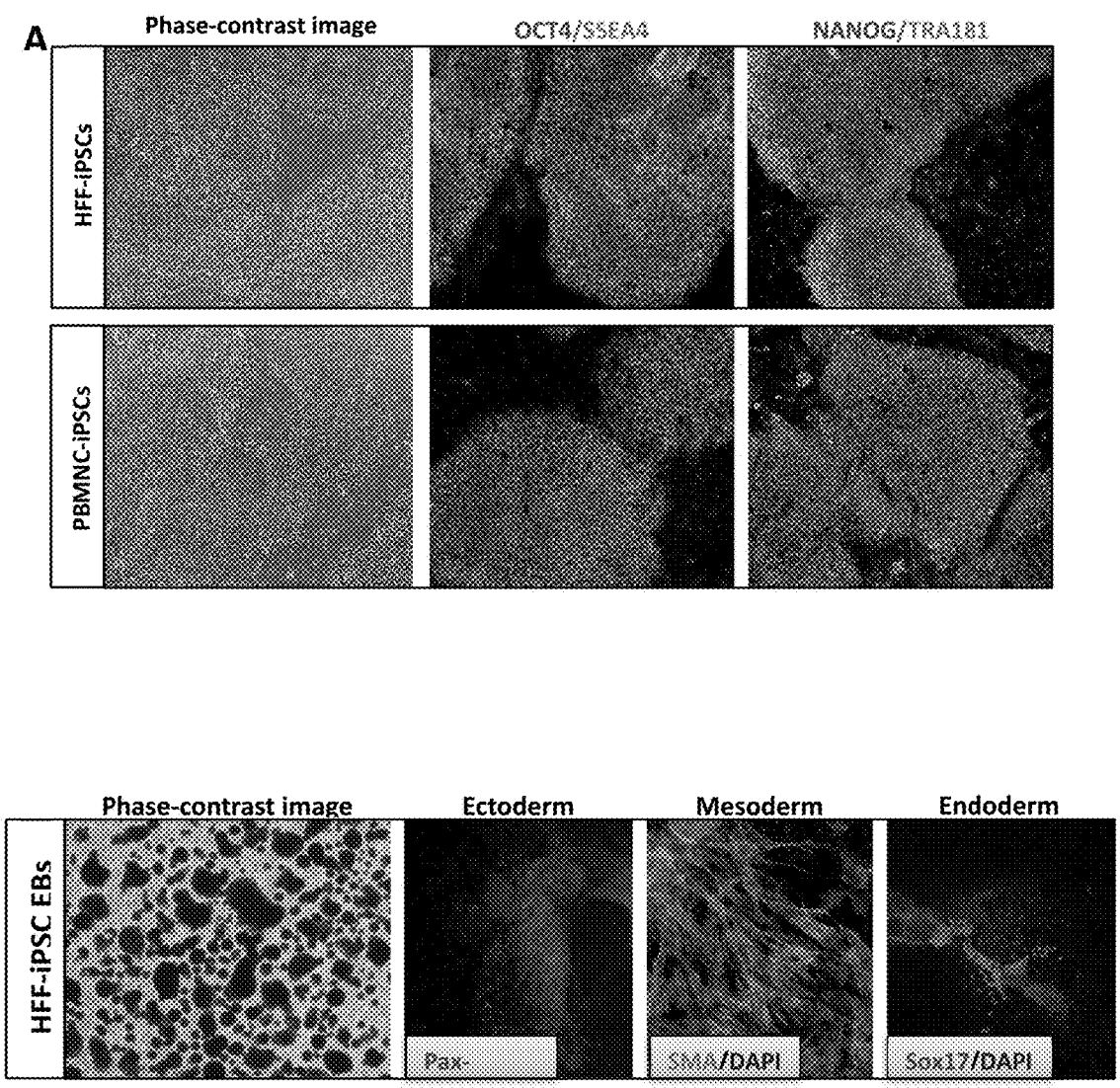
FIG. 4. Characterization of iPSCs derived from reprogramming of HFFs and PBMNCs using CRISPER technology. A. Phase contrast images of HFF-iPSCs and PBMNC-iPSCs taken at passage 5 and 6, respectively. The expression of pluripotency markers in HFF-iPSCs and PBMNC-iPSCs was detected by immunofluorescence staining of OCT4, SSEA4, NANOG and TRA-1-81. B. Phase contrast image of EBs generated by HFF-iPSCs. The cells within the EBs represent the three germ layers—ectoderm, mesoderm and endoderm lineages, as detected by immunofluorescence staining of Pax-6, SMA and Sox17.

The iPSC colonies generated from reprogramming HFFs and PBMNCs using CRISPR technology were manually picked and propagated for 5-6 passages. These iPSC clones were subsequently characterized based on cell morphology, expression of pluripotency markers and multi lineage differentiation potential. Both HFF and PBMNC-derived iPSC clones (HFF-iPSCs and PBMNC-iPSCs, respectively) showed hESC-like morphology, growing as flat colonies with large nucleus-cytoplasmic ratios, defined borders and prominent nuclei (see FIG. 4A). The HFF-iPSCs and PBMNC-iPSCs expressed key pluripotency markers such as OCT4, SSEA4, NANOG and TRA-1-81 (see FIG. 4A). As shown by example of HFF-iPSCs, the iPSCs generated by CRISPR-mediated reprogramming can for embryonic bodies (EBs) and differentiate to cell of the three germ layers—ectoderm, mesoderm and endoderm as indicated by the expression of Pax-6, SMA and Sox17, respectively (see FIG. 4B).

Unless defined otherwise, all technical and scientific terms and any acronyms used herein have the same meanings as commonly understood by one of ordinary skill in the art in the field of this invention. Although any compositions, methods, kits, and means for communicating information similar or equivalent to those described herein can be used to practice this invention, the preferred compositions, methods, kits, and means for communicating information are described herein.

All references cited herein are incorporated herein by reference to the full extent allowed by law. The discussion of those references is intended merely to summarize the assertions made by their authors. No admission is made that any reference (or a portion of any reference) is relevant prior art. Applicants reserve the right to challenge the accuracy and pertinence of any cited reference.

What is claimed is:

1. A method of nuclear reprogramming a mammalian somatic cell, the method comprising: providing a population of mammalian somatic cells comprising an endogenous pluripotency factor gene with:
   a. a first nucleic acid encoding from 2 to 7 distinct guide RNAs (gRNAs), each guide RNA comprising a DNA-binding segment and a polypeptide-binding segment, wherein the DNA-binding segment binds the promoter region of the endogenous pluripotency factor gene; and
   b. a second nucleic acid encoding at least one transcriptional modulator which binds the polypeptide-binding segment of the gRNAs, wherein the transcriptional modulator comprises an enzymatically inactive Cas9 polypeptide (dCas9), wherein the dCas9 is fused to a transcriptional activation domain; and
culturing the mammalian somatic cells for a period of from about 2 to about 14 days, under conditions sufficient to (i) reprogram the mammalian somatic cell to an induced pluripotent stem cell (iPSC), and/or (ii) transdifferentiate the mammalian somatic cell to a target cell different in cell type from said mammalian somatic cell.

2. The method of claim 1, wherein said mammalian somatic cells are human cells.

3. The method of claim 2, wherein said mammalian somatic cells are primary blood cells.

4. The method of claim 3, wherein said blood cells are peripheral blood mononuclear cells (PBMCs) or cord blood mononuclear cells.

5. The method of claim 1, wherein said pluripotency factor gene is selected from the group consisting of oct3/4, sox2, klf4, c-myc, lin28, nanog, glis-1, bcl2, and bclx.

6. The method of claim 1, wherein the transcriptional activation domain is VP64 or p65.

7. The method of claim 1, wherein said population of mammalian somatic cells is further provided with:
   a. a third nucleic acid encoding from 2 to 7 distinct gRNAs, each gRNA comprising a DNA-binding segment and a polypeptide-binding segment, wherein the DNA-binding segment binds the promoter region of a second endogenous pluripotency factor gene; and
   b. a fourth nucleic acid encoding from 2 to 7 distinct gRNAs, each gRNA comprising a DNA-binding segment and a polypeptide-binding segment, wherein the DNA-binding segment binds the promoter region of a third endogenous pluripotency factor gene;
wherein the transcriptional modulator binds the polypeptide-binding segment of the gRNAs encoded by the third and fourth nucleic acids.

8. The method of claim 7, wherein:
the DNA-binding segment of each the gRNAs encoded by the first nucleic acid is complementary to at least a portion of the promoter region of a mammalian oct3/4 gene;
(ii) the DNA-binding segment of each the gRNAs encoded by the third nucleic acid is complementary to at least a portion of the promoter region of a mammalian sox2 gene; and
(iii) the DNA-binding segment of each the gRNAs encoded by the fourth nucleic acid is complementary to at least a portion of the promoter region of a mammalian klf4 gene.

9. A method of nuclear reprogramming a mammalian primary somatic cell, the method comprising:
1) Contacting a population of mammalian primary somatic cells with:
   (a) from two to seven distinct guide RNAs comprising (i) a DNA-binding segment complementary to a portion of a promoter region of a pluripotency factor gene, and (ii) a polypeptide-binding segment; and
   (b) at least one transcriptional modulator comprising:
      (i) dCas9 capable of binding to said polypeptide-binding segment of said guide RNA; and
      (ii) a functional domain selected from a transcriptional activation domain and a repressor domain, and
2) culturing the mammalian somatic cells for a period of from about 2 to about 14 days under conditions sufficient to reprogram the mammalian somatic primary cell to an induced pluripotent stem cell (iPSC).

* * * * *